(12) United States Patent
Stasko et al.

(10) Patent No.: US 11,583,608 B2
(45) Date of Patent: *Feb. 21, 2023

(54) WOUND DRESSINGS, METHODS OF USING THE SAME AND METHODS OF FORMING THE SAME

(71) Applicant: Novan, Inc., Morrisville, NC (US)

(72) Inventors: Nathan Stasko, Chapel Hill, NC (US); Susanne Bauman, Durham, NC (US); Pranav R. Joshi, Bangalore (IN)

(73) Assignee: Novan, Inc., Durham, NC (US)

( * ) Notice: Subject to any disclaimer, the term of this patent is extended or adjusted under 35 U.S.C. 154(b) by 1149 days.

This patent is subject to a terminal disclaimer.

(21) Appl. No.: 15/887,649

(22) Filed: Feb. 2, 2018

(65) Prior Publication Data
US 2018/0214598 A1 Aug. 2, 2018

Related U.S. Application Data

(63) Continuation of application No. 13/256,925, filed as application No. PCT/US2010/046209 on Aug. 20, 2010, now Pat. No. 9,919,072.
(Continued)

(51) Int. Cl.
*A61L 15/22* (2006.01)
*A61L 15/42* (2006.01)
*A61L 15/44* (2006.01)

(52) U.S. Cl.
CPC ............ *A61L 15/44* (2013.01); *A61L 15/225* (2013.01); *A61L 15/425* (2013.01);
(Continued)

(58) Field of Classification Search
CPC ...... A61L 15/44; A61L 15/225; A61L 15/425; A61L 2300/114; A61L 2300/45; A61L 2300/602; A61L 31/145; A61L 31/146; A61L 31/16; A61P 31/00; A61P 17/02; A61K 9/7023; A61K 9/7084;
(Continued)

(56) References Cited

U.S. PATENT DOCUMENTS 4,182,827 A 1/1980 Jones et al.
4,507,466 A 3/1985 Tomalia et al.
(Continued)

FOREIGN PATENT DOCUMENTS

CN 1387542 12/2002
CN 1612804 5/2005
(Continued)

OTHER PUBLICATIONS

Amadeu et al., "Nitric Oxide Donor Improves Healing if Applied on Inflammatory and Proliferative Disease", *Journal of Surgical Research* 149: 84-93 (2008).
(Continued)

*Primary Examiner* — Philip R Wiest
*Assistant Examiner* — Alessandro R Del Priore
(74) *Attorney, Agent, or Firm* — Myers Bigel, P.A.

(57) ABSTRACT

Provided according to some embodiments of the invention are wound dressings that include a polymer matrix and nitric oxide-releasing polysiloxane macromolecules within and/or on the polymer matrix. Also provided are wound dressing kits and methods of using and forming such wound dressings.

36 Claims, 14 Drawing Sheets

Related U.S. Application Data

(60) Provisional application No. 61/235,948, filed on Aug. 21, 2009, provisional application No. 61/235,927, filed on Aug. 21, 2009.

(52) U.S. Cl.
 CPC ...... *A61L 2300/114* (2013.01); *A61L 2300/45* (2013.01); *A61L 2300/602* (2013.01)

(58) Field of Classification Search
 CPC ... A61K 9/7092; A61K 9/0024; A61M 35/00; A61M 35/10; A61M 35/20; A61M 35/25; A61M 35/30; A61M 1/008; A61M 1/0088; A61M 1/009; A61M 27/00; A61F 13/00068; A61F 13/02; A61F 13/0203; A61F 13/0216; A61F 2013/00157; A61F 2013/0017; A61F 2013/00174
 USPC .................. 604/290, 543; 424/426, 401, 448
 See application file for complete search history.

(56) References Cited

U.S. PATENT DOCUMENTS

| | | | |
|---|---|---|---|
| 4,550,126 A | 10/1985 | Lorenz | |
| 4,558,120 A | 12/1985 | Tomalia et al. | |
| 4,568,737 A | 2/1986 | Tomalia et al. | |
| 4,587,329 A | 5/1986 | Tomalia et al. | |
| 4,600,001 A * | 7/1986 | Gilman | A61F 13/023 602/52 |
| 4,631,337 A | 12/1986 | Tomalia et al. | |
| 4,694,064 A | 9/1987 | Tomalia et al. | |
| 4,713,975 A | 12/1987 | Tomalia et al. | |
| 4,737,550 A | 4/1988 | Tomalia | |
| 4,857,599 A | 8/1989 | Tomalia et al. | |
| 4,871,779 A | 10/1989 | Killat et al. | |
| 4,985,023 A | 1/1991 | Blank et al. | |
| 4,990,338 A | 2/1991 | Blank et al. | |
| 5,035,892 A | 7/1991 | Blank et al. | |
| 5,045,322 A | 9/1991 | Blank et al. | |
| 5,061,487 A | 10/1991 | Blank et al. | |
| 5,079,004 A | 1/1992 | Blank et al. | |
| 5,380,758 A | 1/1995 | Stamler et al. | |
| 5,405,919 A | 4/1995 | Keefer et al. | |
| 5,418,301 A | 5/1995 | Hult et al. | |
| 5,428,070 A | 6/1995 | Cooke et al. | |
| 5,504,117 A | 4/1996 | Gorfine | |
| 5,519,020 A | 5/1996 | Smith et al. | |
| 5,525,357 A | 6/1996 | Keefer et al. | |
| 5,574,068 A | 11/1996 | Stamler et al. | |
| 5,593,876 A | 1/1997 | Stamler et al. | |
| 5,599,984 A | 2/1997 | Bianchi et al. | |
| 5,623,981 A | 5/1997 | Saavedra et al. | |
| 5,629,322 A | 5/1997 | Guthikonda et al. | |
| 5,650,442 A | 7/1997 | Mitchell et al. | |
| 5,650,447 A | 7/1997 | Keefer et al. | |
| 5,665,077 A | 9/1997 | Rosen et al. | |
| 5,676,963 A | 10/1997 | Keefer et al. | |
| 5,691,423 A | 11/1997 | Smith et al. | |
| 5,693,676 A | 12/1997 | Gorfine | |
| 5,700,830 A | 12/1997 | Korthuis et al. | |
| 5,718,892 A | 2/1998 | Keefer et al. | |
| 5,726,156 A | 3/1998 | Girten et al. | |
| 5,750,573 A | 5/1998 | Bianchi et al. | |
| 5,753,684 A | 5/1998 | Bianchi et al. | |
| 5,760,001 A | 6/1998 | Girten et al. | |
| 5,770,645 A | 6/1998 | Stamler et al. | |
| 5,786,332 A | 7/1998 | Girten et al. | |
| 5,789,447 A | 8/1998 | Wink, Jr. et al. | |
| 5,797,887 A | 8/1998 | Rosen et al. | |
| 5,810,010 A | 9/1998 | Anbar | |
| 5,814,666 A | 9/1998 | Green et al. | |
| 5,814,667 A | 9/1998 | Mitchell et al. | |
| 5,821,261 A | 10/1998 | Durette et al. | |
| 5,837,736 A | 11/1998 | Mitchell et al. | |
| 5,840,759 A | 11/1998 | Mitchell et al. | |
| 5,849,794 A | 12/1998 | Bianchi et al. | |
| 5,852,058 A | 12/1998 | Cooke et al. | |
| 5,854,289 A | 12/1998 | Bianchi et al. | |
| 5,859,062 A | 1/1999 | Bianchi et al. | |
| 5,861,168 A | 1/1999 | Cooke et al. | |
| 5,863,890 A | 1/1999 | Stamler et al. | |
| 5,891,459 A | 4/1999 | Cooke et al. | |
| 5,891,472 A | 4/1999 | Russell | |
| 5,910,316 A | 6/1999 | Keefer et al. | |
| 5,914,125 A | 6/1999 | Andrews et al. | |
| 5,932,538 A | 8/1999 | Garvey et al. | |
| 5,958,427 A | 9/1999 | Salzman et al. | |
| 5,961,466 A | 10/1999 | Anbar | |
| 5,962,520 A | 10/1999 | Smith et al. | |
| 5,968,001 A | 10/1999 | Freeman | |
| 5,968,528 A | 10/1999 | Deckner et al. | |
| 5,994,294 A | 11/1999 | Garvey et al. | |
| 5,994,444 A | 11/1999 | Trescony et al. | |
| 5,999,843 A | 12/1999 | Anbar | |
| 6,008,255 A | 12/1999 | Bianchi et al. | |
| 6,022,900 A | 2/2000 | Bianchi et al. | |
| 6,035,225 A | 3/2000 | Anbar | |
| 6,043,358 A | 3/2000 | Caldwell et al. | |
| 6,045,827 A | 4/2000 | Russell | |
| 6,070,928 A | 6/2000 | Campbell | |
| 6,087,479 A | 7/2000 | Stamler et al. | |
| 6,103,266 A | 8/2000 | Tapolsky et al. | |
| 6,103,275 A | 8/2000 | Seitz et al. | |
| 6,110,453 A | 8/2000 | Keefer et al. | |
| 6,143,037 A | 11/2000 | Goldstein et al. | |
| 6,147,068 A | 11/2000 | Smith et al. | |
| 6,151,522 A | 11/2000 | Alfano et al. | |
| 6,160,021 A | 12/2000 | Lerner et al. | |
| 6,171,232 B1 | 1/2001 | Papandreou et al. | |
| 6,174,539 B1 | 1/2001 | Stamler et al. | |
| 6,180,082 B1 | 1/2001 | Woltering et al. | |
| 6,180,676 B1 | 1/2001 | Bianchi et al. | |
| 6,190,704 B1 | 2/2001 | Murrell | |
| 6,200,558 B1 | 3/2001 | Saavedra et al. | |
| 6,207,855 B1 | 3/2001 | Toone et al. | |
| 6,218,016 B1 | 4/2001 | Tedeschi et al. | |
| 6,232,336 B1 | 5/2001 | Hrabie et al. | |
| 6,232,434 B1 | 5/2001 | Stamler et al. | |
| 6,238,683 B1 | 5/2001 | Burnett et al. | |
| 6,248,787 B1 | 6/2001 | Bianchi et al. | |
| 6,255,277 B1 | 7/2001 | Stamler et al. | |
| 6,261,594 B1 | 7/2001 | Smith et al. | |
| 6,270,779 B1 | 8/2001 | Fitzhugh et al. | |
| 6,287,601 B1 | 9/2001 | Russell | |
| 6,290,981 B1 | 9/2001 | Keefer et al. | |
| 6,291,424 B1 | 9/2001 | Stamler et al. | |
| 6,294,517 B1 | 9/2001 | Garvey et al. | |
| 6,299,980 B1 | 10/2001 | Shah et al. | |
| 6,323,211 B1 | 11/2001 | Garvey et al. | |
| 6,350,467 B1 | 2/2002 | Demopoulos et al. | |
| 6,352,709 B1 | 3/2002 | Stamler et al. | |
| 6,358,536 B1 | 3/2002 | Thomas | |
| 6,359,167 B2 | 3/2002 | Toone et al. | |
| 6,359,182 B1 | 3/2002 | Stamler et al. | |
| 6,369,071 B1 | 4/2002 | Haj-Yehia | |
| 6,372,733 B1 | 4/2002 | Caldwell et al. | |
| 6,377,321 B1 | 4/2002 | Khan et al. | |
| 6,379,660 B1 | 4/2002 | Saavedra et al. | |
| 6,379,691 B1 | 4/2002 | Tedeschi et al. | |
| 6,391,895 B1 | 5/2002 | Towart et al. | |
| 6,403,759 B2 | 6/2002 | Stamler et al. | |
| 6,410,622 B1 | 6/2002 | Endres | |
| 6,417,162 B1 | 7/2002 | Garvey et al. | |
| 6,432,077 B1 | 8/2002 | Stenzler | |
| 6,433,182 B1 | 8/2002 | Garvey et al. | |
| 6,436,975 B1 | 8/2002 | Del Soldato | |
| 6,441,254 B1 | 8/2002 | Dobert | |
| 6,448,267 B1 | 9/2002 | Anggard et al. | |
| 6,451,337 B1 | 9/2002 | Smith et al. | |
| 6,455,542 B1 | 9/2002 | Anggard et al. | |
| 6,469,065 B1 | 10/2002 | Garvey et al. | |
| 6,471,978 B1 | 10/2002 | Stamler et al. | |
| 6,472,390 B1 | 10/2002 | Stamler et al. | |

(56) References Cited

U.S. PATENT DOCUMENTS

| | | | |
|---|---|---|---|
| 6,474,508 B1 | 11/2002 | Marsh |
| 6,488,951 B2 | 12/2002 | Toone et al. |
| 6,492,405 B2 | 12/2002 | Haj-Yehia |
| 6,511,991 B2 | 1/2003 | Hrabie et al. |
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,338 B1 | 1/2004 | Arnold et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Hermann et al. |
| 6,709,681 B2 | 3/2004 | Benjamin et al. |
| 6,723,703 B2 | 4/2004 | Gaston et al. |
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B1 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,234,079 B2 | 6/2007 | Cheng |
| 7,259,250 B2 | 8/2007 | Stamler et al. |
| 7,279,176 B1 | 10/2007 | West et al. |
| 7,282,519 B2 | 10/2007 | Garvey et al. |
| 7,303,575 B2 * | 12/2007 | Ogle ............... A61B 17/12022 424/422 |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,394,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |
| 7,452,916 B2 | 11/2008 | Cooke |
| 7,468,435 B2 | 12/2008 | Waterhouse et al. |
| 7,485,324 B2 | 2/2009 | Miller et al. |
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,704,518 B2 | 4/2010 | Tamarkin et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,972,137 B2 | 7/2011 | Rosen |
| 7,975,699 B2 | 7/2011 | Hyde et al. |
| 8,003,811 B2 | 8/2011 | Almirante |
| 8,017,074 B2 | 9/2011 | Arnold et al. |
| 8,021,679 B2 | 9/2011 | Chen et al. |
| 8,034,384 B2 | 10/2011 | Meyerhoff et al. |
| 8,043,246 B2 | 10/2011 | Av-Gay et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,529,548 B2 * | 9/2013 | Blott ..................... A61F 13/02 604/543 |
| 8,617,100 B2 | 12/2013 | Eini et al. |
| 8,636,982 B2 | 1/2014 | Tamarkin et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,265,725 B2 | 2/2016 | Tamarkin et al. |
| 9,320,705 B2 | 4/2016 | Tamarkin et al. |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0013304 A1 | 1/2002 | Wilson et al. |

(56) References Cited

U.S. PATENT DOCUMENTS

| | | |
|---|---|---|
| 2002/0018757 A1 | 2/2002 | Harichian et al. |
| 2002/0028223 A1 | 3/2002 | Vatter et al. |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0072550 A1 | 6/2002 | Brady et al. |
| 2002/0090401 A1 | 7/2002 | Tucker et al. |
| 2002/0094985 A1 | 7/2002 | Herrmann et al. |
| 2002/0115586 A1 | 8/2002 | Enikolopov |
| 2002/0122929 A1 | 9/2002 | Simpson et al. |
| 2002/0132234 A1 | 9/2002 | Moskowitz |
| 2002/0133040 A1* | 9/2002 | Woo ................. C08G 18/797 560/157 |
| 2002/0136763 A1 | 9/2002 | Demopoulos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2003/0027844 A1 | 2/2003 | Soldato |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2003/0219854 A1 | 11/2003 | Guarna et al. |
| 2004/0009238 A1 | 1/2004 | Miller et al. |
| 2004/0013747 A1 | 1/2004 | Tucker et al. |
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0228889 A1 | 11/2004 | Cals-Grierson |
| 2004/0254419 A1 | 12/2004 | Wang et al. |
| 2004/0265244 A1 | 12/2004 | Rosen |
| 2005/0036949 A1 | 2/2005 | Tucker et al. |
| 2005/0037093 A1 | 2/2005 | Benjamin |
| 2005/0038473 A1 | 2/2005 | Tamarkin et al. |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0079132 A1 | 4/2005 | Wang et al. |
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171066 A1 | 8/2005 | Bunting et al. |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0232869 A1 | 10/2005 | Tamarkin et al. |
| 2005/0245492 A1 | 11/2005 | Lephart et al. |
| 2005/0249818 A1 | 11/2005 | Sawan et al. |
| 2005/0265958 A1 | 12/2005 | West et al. |
| 2005/0271596 A1 | 12/2005 | Friedman et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0035854 A1 | 2/2006 | Goldstein et al. |
| 2006/0039950 A1 | 2/2006 | Zhou et al. |
| 2006/0058363 A1 | 3/2006 | Wang et al. |
| 2006/0067909 A1 | 3/2006 | West et al. |
| 2006/0095120 A1 | 5/2006 | Hermann |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0153904 A1 | 7/2006 | Smith et al. |
| 2006/0155260 A1 | 7/2006 | Blott et al. |
| 2006/0159726 A1 | 7/2006 | Shell |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0240065 A1 | 10/2006 | Chen |
| 2006/0240070 A1* | 10/2006 | Cromack ............... A61L 29/085 424/426 |
| 2006/0269620 A1 | 11/2006 | Morris et al. |
| 2006/0275218 A1 | 12/2006 | Tamarkin et al. |
| 2006/0286158 A1* | 12/2006 | Calvert Murrell et al. ................ A61K 9/7023 424/449 |
| 2006/0286159 A1 | 12/2006 | Calvert Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059338 A1 | 3/2007 | Knapp |
| 2007/0059351 A1 | 3/2007 | Murrell et al. |
| 2007/0086954 A1 | 4/2007 | Miller |
| 2007/0087025 A1* | 4/2007 | Fitzhugh ............ A61K 2300/00 424/423 |
| 2007/0088345 A1 | 4/2007 | Larson et al. |
| 2007/0089739 A1 | 4/2007 | Fine et al. |
| 2007/0116785 A1 | 5/2007 | Miller |
| 2007/0129690 A1 | 6/2007 | Rosenblatt et al. |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0166255 A1 | 7/2007 | Gupta |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |
| 2007/0275100 A1 | 11/2007 | Miller |
| 2007/0292359 A1 | 12/2007 | Friedman et al. |
| 2007/0292461 A1 | 12/2007 | Tamarkin et al. |
| 2008/0025972 A1 | 1/2008 | Daaka et al. |
| 2008/0031907 A1 | 2/2008 | Tamarkin et al. |
| 2008/0033334 A1* | 2/2008 | Gurtner ................. A61L 15/58 602/50 |
| 2008/0039521 A1 | 2/2008 | Yasuda et al. |
| 2008/0044444 A1 | 2/2008 | Tamarkin et al. |
| 2008/0045909 A1 | 2/2008 | Fossel |
| 2008/0063607 A1 | 3/2008 | Tamarkin et al. |
| 2008/0069779 A1 | 3/2008 | Tamarkin et al. |
| 2008/0069848 A1 | 3/2008 | Peters |
| 2008/0069863 A1 | 3/2008 | Peters |
| 2008/0069905 A1 | 3/2008 | Peters |
| 2008/0071206 A1 | 3/2008 | Peters |
| 2008/0089956 A1 | 4/2008 | Da et al. |
| 2008/0138296 A1 | 6/2008 | Tamarkin et al. |
| 2008/0139450 A1 | 6/2008 | Madhyastha et al. |
| 2008/0145449 A1 | 6/2008 | Stamler |
| 2008/0152596 A1 | 6/2008 | Friedman et al. |

(56) References Cited

U.S. PATENT DOCUMENTS

| | | |
|---|---|---|
| 2008/0166303 A1 | 7/2008 | Tamarkin et al. |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0226751 A1 | 9/2008 | Tucker et al. |
| 2008/0241208 A1 | 10/2008 | Shanley et al. |
| 2008/0253973 A1 | 10/2008 | Tamarkin et al. |
| 2008/0260655 A1 | 10/2008 | Tamarkin et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0292560 A1 | 11/2008 | Tamarkin et al. |
| 2008/0299220 A1 | 12/2008 | Tamarkin et al. |
| 2008/0306012 A1 | 12/2008 | Hrabie et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0029028 A1 | 1/2009 | Garcin et al. |
| 2009/0036491 A1 | 2/2009 | Tucker et al. |
| 2009/0041680 A1 | 2/2009 | Tamarkin et al. |
| 2009/0042819 A1 | 2/2009 | Ellis et al. |
| 2009/0048219 A1 | 2/2009 | Garvey |
| 2009/0068118 A1 | 3/2009 | Eini et al. |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0130029 A1 | 5/2009 | Tamarkin et al. |
| 2009/0131342 A1 | 5/2009 | Ellis |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0175799 A1 | 7/2009 | Tamarkin et al. |
| 2009/0177133 A1 | 7/2009 | Kieswetter et al. |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1* | 8/2009 | Schoenfisch ............ A61P 37/02 424/426 |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1 | 12/2009 | Friedman et al. |
| 2009/0304815 A1 | 12/2009 | Cossu et al. |
| 2009/0317885 A1 | 12/2009 | Mascharak |
| 2010/0003338 A1 | 1/2010 | Hubbell et al. |
| 2010/0015253 A1 | 1/2010 | Benjamin |
| 2010/0016767 A1 | 1/2010 | Jones et al. |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0098733 A1 | 4/2010 | Stasko |
| 2010/0099729 A1 | 4/2010 | Almirante et al. |
| 2010/0112033 A1 | 5/2010 | Ganzarolli de Oliveira et al. |
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0210745 A1* | 8/2010 | McDaniel ............ C09D 5/1668 521/55 |
| 2010/0221195 A1 | 9/2010 | Tamarkin et al. |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0255062 A1 | 10/2010 | Kalivretenos et al. |
| 2010/0256755 A1 | 10/2010 | Chen et al. |
| 2010/0256777 A1 | 10/2010 | Datta et al. |
| 2010/0261930 A1 | 10/2010 | Honda et al. |
| 2010/0262238 A1 | 10/2010 | Chen et al. |
| 2010/0266510 A1 | 10/2010 | Tamarkin et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0297200 A1 | 11/2010 | Schoenfisch et al. |
| 2010/0303891 A1 | 12/2010 | Lee et al. |
| 2010/0310476 A1 | 12/2010 | Tamarkin et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0038965 A1 | 2/2011 | McKay et al. |
| 2011/0045037 A1 | 2/2011 | Tamarkin et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0086234 A1 | 4/2011 | Stasko et al. |
| 2011/0097279 A1 | 4/2011 | Tamarkin et al. |
| 2011/0104240 A1 | 5/2011 | Jones et al. |
| 2011/0106000 A1 | 5/2011 | Jones et al. |
| 2011/0212033 A1 | 9/2011 | Tamarkin et al. |
| 2012/0003293 A1 | 1/2012 | Miller et al. |
| 2012/0141384 A1 | 6/2012 | Tamarkin et al. |
| 2012/0237453 A1 | 9/2012 | Tamarkin et al. |
| 2013/0164225 A1 | 6/2013 | Tamarkin et al. |
| 2013/0189191 A1 | 7/2013 | Tamarkin et al. |

(56) References Cited

U.S. PATENT DOCUMENTS

| | | |
|---|---|---|
| 2013/0189193 A1 | 7/2013 | Tamarkin et al. |
| 2013/0189195 A1 | 7/2013 | Tamarkin et al. |
| 2013/0196951 A1* | 8/2013 | Schoenfisch ........... A61K 33/38 514/63 |
| 2014/0193502 A1 | 7/2014 | Tamarkin et al. |
| 2014/0248219 A1 | 9/2014 | Tamarkin et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0025060 A1 | 1/2015 | Tamarkin et al. |
| 2015/0118164 A1 | 4/2015 | Tamarkin et al. |

FOREIGN PATENT DOCUMENTS

| | | |
|---|---|---|
| CN | 1819848 | 8/2006 |
| CN | 101189032 | 5/2008 |
| CN | 101242815 | 8/2008 |
| CN | 101287505 | 10/2008 |
| EP | 0 805 678 B1 | 10/2003 |
| EP | 0 746 327 B1 | 4/2004 |
| EP | 0 724 436 B1 | 7/2004 |
| EP | 1 411 908 B1 | 5/2005 |
| EP | 1 163 528 B1 | 11/2005 |
| EP | 1 681 068 A1 | 7/2006 |
| EP | 1 690 532 A1 | 8/2006 |
| EP | 1 690 554 A1 | 8/2006 |
| EP | 1 690 557 A1 | 8/2006 |
| EP | 1 690 558 A1 | 8/2006 |
| EP | 1 700 611 A1 | 9/2006 |
| EP | 1 704 876 A1 | 9/2006 |
| EP | 1 704 877 A1 | 9/2006 |
| EP | 1 704 879 A1 | 9/2006 |
| EP | 1 707 224 A1 | 10/2006 |
| EP | 1 728 438 A1 | 12/2006 |
| EP | 1 731 176 A1 | 12/2006 |
| EP | 1 757 278 A1 | 2/2007 |
| EP | 1 764 119 A1 | 3/2007 |
| EP | 1 790 335 A1 | 5/2007 |
| EP | 1 861 130 B1 | 9/2008 |
| EP | 1 343 547 B1 | 4/2009 |
| EP | 1 871 433 B1 | 4/2009 |
| EP | 1 161 248 B1 | 5/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| WO | WO 1995/07691 A1 | 3/1995 |
| WO | WO 1995/10267 A1 | 4/1995 |
| WO | WO 1995/12394 A1 | 5/1995 |
| WO | WO 1995/19767 A1 | 7/1995 |
| WO | WO 1995/22335 A1 | 8/1995 |
| WO | WO 1995/32715 A1 | 12/1995 |
| WO | WO 1996/08966 A1 | 3/1996 |
| WO | WO 1996/13164 A1 | 5/1996 |
| WO | WO 1996/14844 A1 | 5/1996 |
| WO | WO 1996/015781 A1 | 5/1996 |
| WO | WO 1996/15797 A1 | 5/1996 |
| WO | WO 1996/27386 A1 | 9/1996 |
| WO | WO 1996/32118 A1 | 10/1996 |
| WO | WO 1996/32136 A1 | 10/1996 |
| WO | WO 1996/033757 A1 | 10/1996 |
| WO | WO 1996/35416 A1 | 11/1996 |
| WO | WO 1997/16983 A1 | 5/1997 |
| WO | WO 1997/31654 A1 | 9/1997 |
| WO | WO 1997/34014 A1 | 9/1997 |
| WO | WO 1997/047254 A1 | 12/1997 |
| WO | WO 1998/005689 A1 | 2/1998 |
| WO | WO 1998/06389 A1 | 2/1998 |
| WO | WO 1998/08482 A2 | 3/1998 |
| WO | WO 1998/08482 A3 | 3/1998 |
| WO | WO 1998/08496 A1 | 3/1998 |
| WO | WO 1998/13358 A1 | 4/1998 |
| WO | WO 1998/19996 A1 | 5/1998 |
| WO | WO 1998/020015 A1 | 5/1998 |
| WO | WO 1998/22090 A1 | 5/1998 |
| WO | WO 1998/29101 A1 | 7/1998 |
| WO | WO 1998/42661 A1 | 10/1998 |
| WO | WO 1999/00070 A1 | 1/1999 |
| WO | WO 1999/01427 A2 | 1/1999 |
| WO | WO 1999/18949 A1 | 4/1999 |
| WO | WO 1999/22729 A1 | 5/1999 |
| WO | WO 1999/33823 A1 | 7/1999 |
| WO | WO 1999/37616 A1 | 7/1999 |
| WO | WO 1999/44595 A2 | 9/1999 |
| WO | WO 1999/44595 A3 | 9/1999 |
| WO | WO 1999/51221 A1 | 10/1999 |
| WO | WO 1999/67210 A1 | 12/1999 |
| WO | WO 1999/67296 A1 | 12/1999 |
| WO | WO 2000/03640 A1 | 1/2000 |
| WO | WO 2000/06151 A1 | 2/2000 |
| WO | WO 2000/30658 A1 | 6/2000 |
| WO | WO 2000/33877 A1 | 6/2000 |
| WO | WO 2000/56333 A1 | 9/2000 |
| WO | WO 2000/59304 A1 | 10/2000 |
| WO | WO 2000/76318 A1 | 12/2000 |
| WO | WO 2001/12067 A1 | 2/2001 |
| WO | WO 2001/015738 A2 | 3/2001 |
| WO | WO 2001/015738 A3 | 3/2001 |
| WO | WO 2001/26702 A2 | 4/2001 |
| WO | WO 2001/26702 A3 | 4/2001 |
| WO | WO 2001/45732 A2 | 6/2001 |
| WO | WO 2001/45732 A3 | 6/2001 |
| WO | WO 2001/70199 A1 | 9/2001 |
| WO | WO 2001/085227 A2 | 11/2001 |
| WO | WO 2001/085227 A3 | 11/2001 |
| WO | WO 2001/089572 A1 | 11/2001 |
| WO | WO 2002/017880 A2 | 3/2002 |
| WO | WO 2002/017880 A3 | 3/2002 |
| WO | WO 2002/017881 A2 | 3/2002 |
| WO | WO 2002/017881 A3 | 3/2002 |
| WO | WO 2002/020026 A2 | 3/2002 |
| WO | WO 2002/020026 A3 | 3/2002 |
| WO | WO 2002/032418 A1 | 4/2002 |
| WO | WO 2002/034705 A2 | 5/2002 |
| WO | WO 2002/043786 A2 | 6/2002 |
| WO | WO 2002/043786 A3 | 6/2002 |
| WO | WO 2002/047675 A1 | 6/2002 |
| WO | WO 2002/051353 A2 | 7/2002 |
| WO | WO 2002/051353 A3 | 7/2002 |
| WO | WO 2002/056864 A2 | 7/2002 |
| WO | WO 2002/056864 A3 | 7/2002 |
| WO | WO 2002/056874 A2 | 7/2002 |
| WO | WO 2002/056904 A1 | 7/2002 |
| WO | WO 2002/070496 A1 | 9/2002 |
| WO | WO 2002/076395 A2 | 10/2002 |
| WO | WO 2002/076395 A3 | 10/2002 |
| WO | WO 2003/004097 A1 | 1/2003 |
| WO | WO 2003/006427 A1 | 1/2003 |
| WO | WO 2003/015605 A2 | 2/2003 |
| WO | WO 2003/015605 A3 | 2/2003 |
| WO | WO 2003/017989 A1 | 3/2003 |
| WO | WO 2003/026717 A1 | 4/2003 |
| WO | WO 2003/030659 A1 | 4/2003 |
| WO | WO 2003/041713 A1 | 5/2003 |
| WO | WO 2003/047636 A2 | 6/2003 |
| WO | WO 2003/047636 A3 | 6/2003 |
| WO | WO 2003/080039 A1 | 10/2003 |
| WO | WO 2003/092763 A1 | 11/2003 |
| WO | WO 2003/095398 A2 | 11/2003 |
| WO | WO 2003/095398 A3 | 11/2003 |
| WO | WO 2004/009066 A1 | 1/2004 |
| WO | WO 2004/009253 A1 | 1/2004 |
| WO | WO 2004/011421 A1 | 2/2004 |
| WO | WO 2004/012874 A1 | 2/2004 |
| WO | WO 2004/037798 A1 | 5/2004 |
| WO | WO 2004/039313 A2 | 5/2004 |
| WO | WO 2004/039313 A3 | 5/2004 |
| WO | WO 2004/060283 A2 | 7/2004 |
| WO | WO 2004/064767 A2 | 8/2004 |
| WO | WO 2004/064767 A3 | 8/2004 |
| WO | WO 2004/087212 A2 | 10/2004 |
| WO | WO 2004/098538 A2 | 11/2004 |

(56) References Cited

FOREIGN PATENT DOCUMENTS

| | | |
|---|---|---|
| WO | WO 2004/098538 A3 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/011575 A3 | 2/2005 |
| WO | WO 2005/030118 A2 | 4/2005 |
| WO | WO 2005/030118 A3 | 4/2005 |
| WO | WO 2005/030135 A2 | 4/2005 |
| WO | WO 2005/030135 A3 | 4/2005 |
| WO | WO 2005/030147 A2 | 4/2005 |
| WO | WO 2005/030147 A3 | 4/2005 |
| WO | WO 2005/034860 A2 | 4/2005 |
| WO | WO 2005/034860 A3 | 4/2005 |
| WO | WO 2005/039664 A2 | 5/2005 |
| WO | WO 2005/039664 A3 | 5/2005 |
| WO | WO 2005/067986 A1 | 7/2005 |
| WO | WO 2005/070006 A2 | 8/2005 |
| WO | WO 2005/070006 A3 | 8/2005 |
| WO | WO 2005/070008 A2 | 8/2005 |
| WO | WO 2005/070008 A3 | 8/2005 |
| WO | WO 2005/070874 A1 | 8/2005 |
| WO | WO 2005/070883 A1 | 8/2005 |
| WO | WO 2005/072819 A1 | 8/2005 |
| WO | WO 2005/077962 A2 | 8/2005 |
| WO | WO 2005/077962 A3 | 8/2005 |
| WO | WO 2005/081752 A2 | 9/2005 |
| WO | WO 2005/081752 A3 | 9/2005 |
| WO | WO 2005/081964 A2 | 9/2005 |
| WO | WO 2005/094913 A1 | 10/2005 |
| WO | WO 2005/102282 A1 | 11/2005 |
| WO | WO 2005/107384 A2 | 11/2005 |
| WO | WO 2005/107384 A3 | 11/2005 |
| WO | WO 2005/112954 A1 | 12/2005 |
| WO | WO 2005/115440 A2 | 12/2005 |
| WO | WO 2005/115440 A3 | 12/2005 |
| WO | WO 2005/120493 A1 | 12/2005 |
| WO | WO 2006/023693 A2 | 3/2006 |
| WO | WO 2006/023693 A3 | 3/2006 |
| WO | WO 2006/037105 A2 | 4/2006 |
| WO | WO 2006/037105 A3 | 4/2006 |
| WO | WO 2006/041855 A2 | 4/2006 |
| WO | WO 2006/041855 A3 | 4/2006 |
| WO | WO 2006/045639 A1 | 5/2006 |
| WO | WO 2006/055542 A2 | 5/2006 |
| WO | WO 2006/055542 A3 | 5/2006 |
| WO | WO 2006/058318 A2 | 6/2006 |
| WO | WO 2006/064056 A2 | 6/2006 |
| WO | WO 2006/066362 A1 | 6/2006 |
| WO | WO 2006/084909 A1 | 8/2006 |
| WO | WO 2006/084910 A1 | 8/2006 |
| WO | WO 2006/084911 A1 | 8/2006 |
| WO | WO 2006/084912 A1 | 8/2006 |
| WO | WO 2006/084913 A1 | 8/2006 |
| WO | WO 2006/084914 A1 | 8/2006 |
| WO | WO 2006/100155 A1 | 8/2006 |
| WO | WO 2006/095193 A2 | 9/2006 |
| WO | WO 2006/095193 A3 | 9/2006 |
| WO | WO 2006/096572 A1 | 9/2006 |
| WO | WO 2006/097348 A1 | 9/2006 |
| WO | WO 2006/099058 A2 | 9/2006 |
| WO | WO 2006/099058 A3 | 9/2006 |
| WO | WO 2006/100154 A1 | 9/2006 |
| WO | WO 2006/100156 A2 | 9/2006 |
| WO | WO 2006/100156 A3 | 9/2006 |
| WO | WO 2006/122960 A1 | 11/2006 |
| WO | WO 2006/122961 A1 | 11/2006 |
| WO | WO 2006/125016 A1 | 11/2006 |
| WO | WO 2006/125262 A1 | 11/2006 |
| WO | WO 2006/127591 A2 | 11/2006 |
| WO | WO 2006/127591 A3 | 11/2006 |
| WO | WO 2006/128121 A2 | 11/2006 |
| WO | WO 2006/128742 A2 | 12/2006 |
| WO | WO 2006/128742 A3 | 12/2006 |
| WO | WO 2006/128743 A1 | 12/2006 |
| WO | WO 2006/130982 A1 | 12/2006 |
| WO | WO 2007/003028 A1 | 1/2007 |
| WO | WO 2007/005910 A2 | 1/2007 |
| WO | WO 2007/005910 A3 | 1/2007 |
| WO | WO 2007/007208 A2 | 1/2007 |
| WO | WO 2007/012165 A1 | 2/2007 |
| WO | WO 2007/016677 A2 | 2/2007 |
| WO | WO 2007/016677 A3 | 2/2007 |
| WO | WO 2007/023005 A1 | 3/2007 |
| WO | WO 2007/023396 A2 | 3/2007 |
| WO | WO 2007/024501 A2 | 3/2007 |
| WO | WO 2007/024501 A3 | 3/2007 |
| WO | WO 2007/027859 A1 | 3/2007 |
| WO | WO 2007/028657 A1 | 3/2007 |
| WO | WO 2007/030266 A2 | 3/2007 |
| WO | WO 2007/030266 A3 | 3/2007 |
| WO | WO 2007/050379 A2 | 5/2007 |
| WO | WO 2007/050379 A3 | 5/2007 |
| WO | WO 2007/053292 A2 | 5/2007 |
| WO | WO 2007/053578 A2 | 5/2007 |
| WO | WO 2007/053578 A3 | 5/2007 |
| WO | WO 2007/054373 A1 | 5/2007 |
| WO | WO 2007/054818 A2 | 5/2007 |
| WO | WO 2007/057763 A2 | 5/2007 |
| WO | WO 2007/057763 A3 | 5/2007 |
| WO | WO 2007/059311 A2 | 5/2007 |
| WO | WO 2007/059311 A3 | 5/2007 |
| WO | WO 2007/064895 A2 | 6/2007 |
| WO | WO 2007/064895 A3 | 6/2007 |
| WO | WO 2007/067477 A1 | 6/2007 |
| WO | WO 2007/084533 A2 | 7/2007 |
| WO | WO 2007/084533 A3 | 7/2007 |
| WO | WO 2007/086884 A2 | 8/2007 |
| WO | WO 2007/086884 A3 | 8/2007 |
| WO | WO 2007/088050 A2 | 8/2007 |
| WO | WO 2007/088050 A3 | 8/2007 |
| WO | WO 2007/088123 A2 | 8/2007 |
| WO | WO 2007/088123 A3 | 8/2007 |
| WO | WO 2007/092284 A2 | 8/2007 |
| WO | WO 2007/092284 A3 | 8/2007 |
| WO | WO 2007/100910 A2 | 9/2007 |
| WO | WO 2007/100910 A3 | 9/2007 |
| WO | WO 2007/103190 A2 | 9/2007 |
| WO | WO 2007/103190 A3 | 9/2007 |
| WO | WO 2007/127725 A2 | 11/2007 |
| WO | WO 2007/127725 A3 | 11/2007 |
| WO | WO 2007/133922 A2 | 11/2007 |
| WO | WO 2007/133922 A3 | 11/2007 |
| WO | WO 2007/143185 A2 | 12/2007 |
| WO | WO 2007/143185 A3 | 12/2007 |
| WO | WO 2007/149437 A1 | 12/2007 |
| WO | WO 2007/149520 A2 | 12/2007 |
| WO | WO 2007/149520 A3 | 12/2007 |
| WO | WO 2008/005313 A2 | 1/2008 |
| WO | WO 2008/005313 A3 | 1/2008 |
| WO | WO 2008/013633 A2 | 1/2008 |
| WO | WO 2008/013633 A3 | 1/2008 |
| WO | WO 2008/020218 A1 | 2/2008 |
| WO | WO 2008/027203 A2 | 3/2008 |
| WO | WO 2008/027203 A3 | 3/2008 |
| WO | WO 2008/032212 A2 | 3/2008 |
| WO | WO 2008/038140 A2 | 4/2008 |
| WO | WO 2008/038147 A2 | 4/2008 |
| WO | WO 2008/062160 A1 | 5/2008 |
| WO | WO 2008/071242 A1 | 6/2008 |
| WO | WO 2008/088507 A2 | 7/2008 |
| WO | WO 2008/088507 A3 | 7/2008 |
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/110872 A2 | 9/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |

(56) References Cited

FOREIGN PATENT DOCUMENTS

| | | |
|---|---|---|
| WO | WO 2008/150505 A1 | 12/2008 |
| WO | WO 2008/152444 A2 | 12/2008 |
| WO | WO 2008/157393 A1 | 12/2008 |
| WO | WO 2009/007785 A2 | 1/2009 |
| WO | WO 2009/014616 A1 | 1/2009 |
| WO | WO 2009/014829 A2 | 1/2009 |
| WO | WO 2009/014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009/056991 A2 | 5/2009 |
| WO | WO 2009/064861 A2 | 5/2009 |
| WO | WO 2009/064861 A3 | 5/2009 |
| WO | WO 2009/072007 A2 | 6/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/087578 A2 | 7/2009 |
| WO | WO 2009/088433 A1 | 7/2009 |
| WO | WO 2009/090495 A2 | 7/2009 |
| WO | WO 2009/098113 A1 | 8/2009 |
| WO | WO 2009/098595 A2 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 2010/033242 A3 | 3/2010 |
| WO | WO 2010/045415 A2 | 4/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |

OTHER PUBLICATIONS

Ashutosh et al., "Use of nitric oxide inhalation in chronic obstructive pulmonary disease" Thorax 55:109-113 (2000).

Azizzadeh et al., Nitric Oxide Improves Cisplatin Cytotoxicity in Head and Neck Squamous Cell Carcinoma, The Laryngoscope 111: 1896-1900 (2001).

Barbe et al. "Silica Particles: A Novel Drug-Delivery System" Advanced Materials 16(21):1959-1965 (2004).

Barraud et al., "Involvement of Nitric Oxide in Biofilm Dispersal of Pseudomonas aeruginosa," Journal of Bacteriology, 2006, 188(21): 7344-7353.

Barst et al., "Clinical perspectives with long-term pulsed inhaled nitric oxide for the treatment of pulmonary arterial hypertension", Pulmonary Circulation, 2012, 2(2): 139-147.

Benz et al., "Effect of Nitric Oxide in Ischemia/Reperfusion of the Pancreas", Journal of Surgical Research, 2002, 106: 46-53.

Bian et al., "Vascular System: Role of Nitric Oxide in Cardiovascular Diseases", The Journal of Clinical Hypertension, 2008, 10(4): 304-310.

Bloch et al., "Inhaled NO as a therapeutic agent", Cardiovascular Research, 2007, 75: 339-348.

Bohl Masters et al. "Effects of nitric oxide releasing vinyl poly(vinyl alcohol) hydrogel dressings on dermal wound healing in diabetic mice" Wound Repair and Regeneration, 2002, 10(5): 286-294.

Bonavida et al., "Therapeutic potential of nitric oxide in cancer", Drug Resistance Updates, 2006, 9: 157-173.

Bonavida et al., "Novel therapeutic applications of nitric oxide donors in cancer: Roles in chemo- and immunosensitization to apoptosis and inhibition of metastases", Nitric Oxide, 2008, 152-157.

Boykin et al., "HBO Mediates Increased Nitric Oxide Production Associated With Wound Healing" Wound Repair and Regeneration 12(2):A15 (Abstract 054) (2004).

Boykin Jr., Joseph V., "Wound Nitric Oxide Bioactivity: A Promising Diagnostic Indicator for Diabetic Foot Ulcer Management", Journal of Wound, Ostomy & Continence Nursing 37(1):25-32 (2010).

Brennan et al., "The role of nitric oxide in oral diseases", Archives of Oral Biology, 2003, 48: 93-100.

Bruch-Gerharz et al. "Nitric Oxide in Human Skin: Current Status and Future Prospects" The Journal of Investigative Dermatology, 1998, 110(1): 1-7.

Cals-Grierson et al., "Nitric oxide function in the skin", Nitric Oxide, 2004, 10: 179-193.

Carlsson et al., "Intravesical Nitric Oxide Delivery for Prevention of Catheter-Associated Urinary Tract Infections", Antimicrobial Agents and Chemotherapy, 2005, 49(6): 2352-2355.

Coban et al. "The Effect of Nitric Oxide Combined with Fluoroquinolones against Salmonellaenterica Serovar Typhimurium in Vitro" Mem. Inst. Oswaldo Cruz, 2003, 98(3): 419-423.

Davies et al. "Chemistry of the Diazeniumdiolates. 2. Kinetics and Mechanism of Dissociation to Nitric Oxide in Aqueous Solution" Journal of the American Chemical Society 123(23):5473-5481 (2001).

De Groote et al. "NO Inhibitors: Antimicrobial Properties of Nitric Oxide" Clinical Infectious Diseases, 1995, 21(Suppl. 2): S162-S165.

Dobmeier et al. "Antibacterial Properties of Nitric Oxide-Releasing Sol-Gel Microarrays" Biomacromolecules 5(6):2493-2495 (2004).

Examination Report corresponding to European Patent Application No. 10747385.2 (dated Sep. 2, 2014).

Examination Report corresponding to European Patent Application No. 10747385.2 (5 pages) (dated Jul. 21, 2016).

Fang, Ferric, "Mechanisms of Nitric Oxide-related Antimicrobial Activity", Journal of Clinical Investigation, 1997, 99(12): 2818-2825.

Farias-Eisner et al., "The Chemistry and Tumoricidal Activity of Nitric Oxide/Hydrogen Peroxide and the Implications to Cell Resistance/Susceptibility", The Journal of Biological Chemistry, 1996, 271(11): 6144-6151.

Frederiksen et al., "Chemosensitization of Cancer In vitro and In vivo by Nitric Oxide Signaling", Clinical Cancer Research, 2007, 13: 2199-2206.

Ghaffari et al., "Potential application of gaseous nitric oxide as a topical antimicrobial agent", Nitric Oxide, 2006, 14(1): 21-29.

Gupta et al., "Bioactive materials for biomedical applications using sol-gel technology", Biomedical Materials 3: 1-15 (2008).

Hatton et al. "Past, Present, and Future of Periodic Mesoporous Organosilicas—The PMOs" Accounts of Chemical Research 38(4):305-312 (2005).

Herman et al., "Therapeutic potential of nitric oxide donors in the prevention and treatment of atherosclerosis", European Heart Journal, 2005, 26: 1945-1955.

Hetrick et al., "Reducing Implant-Related Infections: Active Release Strategies", Chemical Society Reviews 36: 780-789 (2006).

Hetrick et al., "Antibacterial Nitric Oxide-Releasing Xerogels: Cell Viability and Parallel Plate Flow Cell Adhesion Studies", Biomaterials 28(11): 1948-1956 (2007).

Hetrick et al., "Bactericidal Efficacy of Nitric Oxide-Releasing Silica Nanoparticles", ACS Nano 2(2): 235-246 (2008).

Hetrick et al., "Anti-biofilm efficacy of nitric oxide-releasing silica nanoparticles", Biomaterials, 2009, 30: 2782-2789.

Hirst et al., "Targeting nitric oxide for cancer therapy", Journal of Pharmacy and Pharmacology, 2007, 59: 3-13.

(56) References Cited

OTHER PUBLICATIONS

Howlin et al., "Nitric oxide-mediated dispersal and enhanced antibiotic sensitivity in pseudomonas aeruginosa biofilms from the cystic fibrosis lung", *Archives of Disease In Childhood*, 2011, 96: A45.
Hrabie et al., "Chemistry of the nitric oxide-releasing diazeniumdiolate ('nitrosohydroxylamine') functional group and its oxygen-substituted derivatives", *Chemical Reviews* 102: 1135-1154 (2002).
Huerta et al., "Nitric oxide donors: Novel cancer therapeutics (Review)", *International Journal of Oncology*, 2008, 33: 909-927.
International Preliminary Report on Patentability Corresponding to International Application No. PCT/US2009/005643; dated Apr. 28, 2011.
International Preliminary Reporton Patentability Corresponding to International Application No. PCT/US2010/046209; dated Mar. 1, 2012.
International Search Report and the Written Opinion of the International Searching Authority Corresponding to International Application No. PCT/US2009/005643; dated May 24, 2010.
International Search Report and the Written Opinion of the International Searching Authority Corresponding to International Application No. PCT/US2010/046173; dated Dec. 6, 2010.
International Search Report and the Written Opinion of the International Searching Authority Corresponding to International Application No. PCT/US2010/052460; dated Jan. 24, 2011.
International Search Report and the Written Opinion of the International Searching Authority Corresponding to International Application No. PCT/US2010/046209; dated May 23, 2011.
Iwakiri et al., "Synthesis of amphiphilic polysiloxanes and their properties for formation of nano-aggregates", *Colloid and Polymer Science* 287: 577-582 (2009).
Johnson et al., "Reduced ischemia/reperfusion injury via glutathione-initiated nitric oxide-releasing dendrimers", *Nitric Oxide*, 2010, 22(1): 30-36.
Jones et al. "Antimicrobial properties of nitric oxide and its application in antimicrobial formulations and medical devices", *Applied Microbiology and Biotechnology*, 2010, 88: 401-407.
Kiziltepe et al., "JS-K, a GST-activated nitric oxide generator, induces DNA double-strand breaks, activates DNA damage response pathways, and induces apoptosis in vitro and in vivo in human multiple myeloma cells", *Blood*, 2007, 110: 709-718.
Lamas et al., "Nitric oxide signaling comes of age: 20 years and thriving", *Cardiovascular Research*, 2007, 75: 207-209.
Lin et al., "Structural and Morphological Control of Cationic Surfactant-Templated Mesoporous Silica", *Accounts of Chemical Research*, 2002, 35(11): 927-935.
Liu et al., "Nitric Oxide Inhalation Improves Microvascular Flow and Decreases Infarction Size After Myocardial Ischemia and Reperfusion", *Journal of the American College of Cardiology*, 2007, 50(8): 808-817.
Living Water Acid-Alkaline Balance http://www.livinqwaterhealthsolutions.com/Articles/alkalize.php, accessed online: Nov. 3, 2011.
Luo et al., "Nitric oxide: a newly discovered function on wound healing", *Acta Pharmacologica Sinica*, 2005, 26(3): 259-264.
Marxer et al., "Sol-Gel Derived Nitric Oxide-Releasing Oxygen Sensors", *The Analyst*, 2005, 130(2): 206-212.
Mcelhaney-Feser et al., "Synergy of Nitric Oxide and Azoles against Candida Species In Vitro," *Antimicrobial Agents And Chemotherapy* 42(9) 2342-2346 (1998).
Mcgrowder et al., "Therapeutic Uses of Nitric Oxide-donating Drugs in the Treatment of Cardiovascular Diseases", *International Journal of Pharmacology*, 2006, 2(4): 366-373.
Nablo et al., "Inhibition of Implant-Associated Infections via Nitric Oxide Release", *Biomaterials*, 2005, 26(34): 6984-6990.
Nablo et al., "Nitric Oxide-Releasing Sol-Gels as Antibacterial Coatings for Orthopedic Implants", *Biomaterials*, 2005, 26(8): 917-924.
Napoli et al., "Nitric oxide and atherosclerosis: An update", *Nitric Oxide*, 2006, 15(4): 265-279.

Office Action corresponding to Canadian Application No. 2,606,565 (dated Mar. 27, 2013).
Office Action corresponding to Chinese Patent Application No. 201080047383.8 (23 pages) (dated Oct. 17, 2013).
Office Action corresponding to Chinese Patent Application No. 201080047383.8 (dated Jun. 10, 2014).
Office Action corresponding to Chinese Patent Application No. 201080047383.8 (dated Dec. 2, 2014).
Office Action corresponding to Chinese Patent Application No. 201080047383.8 (dated May 13, 2015).
Office Action corresponding to Chinese Patent Application No. 201080047383.8 (19 pages) (dated Oct. 27, 2015).
Phillips et al., "Nitric Oxide Mechanism of Protection in Ischemia and Reperfusion Injury", *Journal of Investigative Surgery*, 2009, 22: 46-55.
Pulfer et al., "Incorporation of Nitric Oxide-Releasing Crosslinked Polyethyleneimine Microspheres Into Vascular Grafts", *Journal of Biomedical Materials Research*, 1997, 37(2): 182-189.
Reynolds et al., "Nitric Oxide-Releasing Hydrophobic Polymers: Preparation, Characterization, and Potential Biomedical Applications", *Free Radical Biology and Medicine*, 2004, 37(7): 926-936.
Robson, Martin, "Wound Infection: A Failure of Wound Healing Caused by an Imbalance of Bacteria," *Surgical Clinics of North America*, 1997, 77(3): 637-50.
Rothrock et al., "Synthesis of Nitric Oxide-Releasing Gold Nanoparticles", *Journal of the American Chemical Society*, 2005, 127(26): 9362-9363.
Saavedra et al., "Esterase-Sensitive Nitric Oxide Donors of the Diazeniumdiolate Family: In Vitro Antileukemic Activity", *Journal of Medicinal Chemistry*, 2000, 43, 261-269.
Salivary pH Testing: https://allicincenter.com/pdf/ph_testing.pdf, Accessed online Nov. 3, 2011.
Sangster, James "Octanol-Water Partition Coefficients of Simple Organic Compounds" *Journal of Physical and Chemical Reference Data* 18(3): 1111-1227 (1989).
Saral et al., "The Equilibrium Between Endothelin-1/Nitric Oxide in Acne Vulgaris," *Istanbul Tip Fakultesi Dergisi Cilt*, 2008, 71(4): 101-105.
Sato et al., "Dynamic Aspect of Reactive Oxygen and Nitric Oxide in Oral Cavity", *Journal of Clinical Biochemistry and Nutrition*, 2008, 42: 8-13.
Schaffer et al., "Diabetes-impaired healing and reduced wound nitric oxide synthesis: A possible pathophysiologic correlation", *Surgery*, 1997, 121(5):513-519.
Schairer et al., "The potential of nitric oxide releasing therapies as antimicrobial agents", *Virulence*, 2012, 3(3): 271-279.
Schulz et al., "Nitric oxide in myocardial ischemia/reperfusion injury", *Cardiovascular Research*, 2004, 61: 402-413.
Schwentker et al., "Nitric oxide and wound repair: role of cytokines?" *Nitric Oxide*, 2002, 7(1): 1-10.
Shi et al. "The role of iNOS in wound healing", *Surgery*, 2001, 130(2): 225-229.
Shin et al. "Nitric Oxide-Releasing Sol-Gel Particle/Polyurethane Glucose Biosensors", *Analytical Chemistry* 76: 4543-4549 (2004).
Shin et al. "Synthesis of Nitric Oxide-releasing Silica Nanoparticles" *Journal of the American Chemical Society* 129:4612-4619 (2007).
Simeone et al., "N-(4-Hydroxyphenyl) retinamide and nitric oxide pro-drugs exhibit apoptotic and anti-invasive effects against bone metastatic breast cancer cells" *Carcinogenesis*, 2006, 27(3): 568-577.
Siriussawakul et al., "Role of nitric oxide in hepatic ischemia-reperfusion injury", *World Journal of Gastroenterology*, 2010, 16(48): 6079-6086.
Slowing et al. "Mesoporous silica nanoparticles as controlled release drug delivery and gene transfection carriers", *Advanced Drug Delivery Reviews*, 2008, 60: 1278-1288.
Stasko et al., "Dendrimers as a Scaffold for Nitric Oxide Release", *Journal of the American Chemical Society*, 2005, 128: 8265-8271.
Stein et al., "Hybrid Inorganic Organic Mesoporous Silicates Nanoscopic Reactors Coming of Age", *Advanced Materials*, 2000, 12(19): 1403-1419.

(56) References Cited

OTHER PUBLICATIONS

Stevens et al. "Nitric Oxide-Releasing Silica Nanoparticle Inhibition of Ovarian Cancer Cell Growth" *Molecular Pharmaceutics* 7(3):775-785 (2010).
Summersgill et al., "Killing of Legionella pneumophila by nitric oxide in γ-interferon-activated macrophages", *Journal of Leukocyte Biology*, 1992, 52: 625-629.
Supplementary European Search Report corresponding to European Patent Application No. 06771501.1 (dated Dec. 14, 2012).
Tang et al. "Synthesis of Beta-Lactamase Activated Nitric Oxide Donors" *Bioorganic & Medicinal Chemistry Letters* 13:1687-1690 (2003).
Terpolilli et al. "Inhalation of Nitric Oxide Prevents Ischemic Brain Damage in Experimental Stroke by Selective Dilatation of Collateral Arterioles" *Circulation Research* 110:727-738 (2012).
Thomas et al. "Hypoxic inducible factor 1α, extracellular signal-regulated kinase, and p53 are regulated by distinct threshold concentrations of nitric oxide" *PNAS* 101(24): 8894-8899 (2004).
Weller, Richard, "Nitric oxide donors and the skin: useful therapeutic agents?" *Clinical Science*, 2003, 105: 533-535.
Wink et al. "The multifaceted roles of nitric oxide in cancer" *Carcinogenesis*, 1998, 19(5):711-721.
Witte et al., "Nitric oxide enhances experimental wound healing in diabetes", *British Journal of Surgery*, 2002, 89: 1594-1601.
Witte et al., "Role of nitric oxide in wound repair", *The American Journal of Surgery*, 2002, 183(4): 406-412.
Yetik-Anacak et al. "Nitric oxide and the endothelium: History and impact on cardiovascular disease", *Vascular Pharmacology* 45(5): 268-276 (2006).
Zhang et al., "Nitric Oxide-Releasing Fumed Silica Particles: Synthesis, Characterization, and Biomedical Application", *Journal of the American Chemical Society* 125: 5015-5024 (2003).
Zhu et al. "Corrosion protection of metals by water-based silane mixtures of bis-[trimethoxysilylpropyl]amine and vinyltriacetoxysilane" *Progress in Organic Coatings* 49: 42-53 (2004).
Zhu et al. "Nitric Oxide Accelerates the Recovery from Burn Wounds", *World Journal of Surgery* 31: 624-631 (2007).
Zhu et al. "Effects of Nitric Oxide on Skin Burn Wound Healing" *Journal of Burn Care & Research* 29(5): 804-814 (2008).

\* cited by examiner

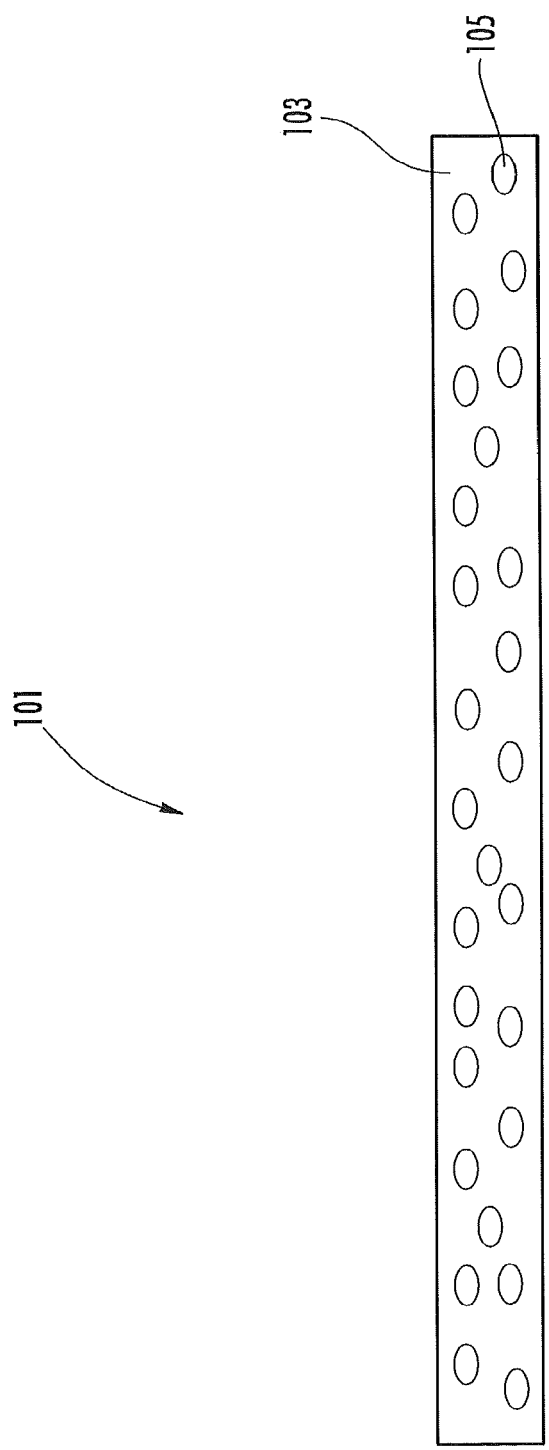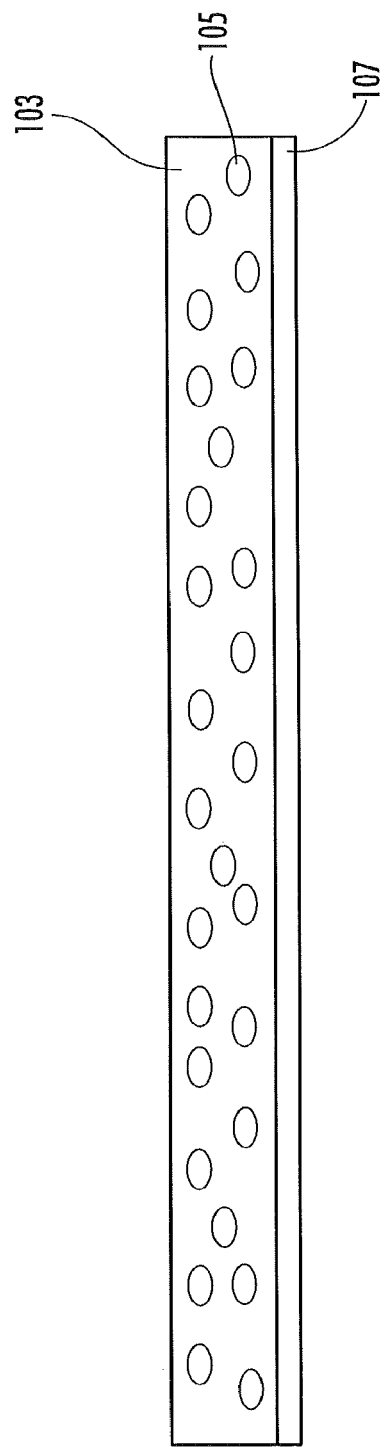

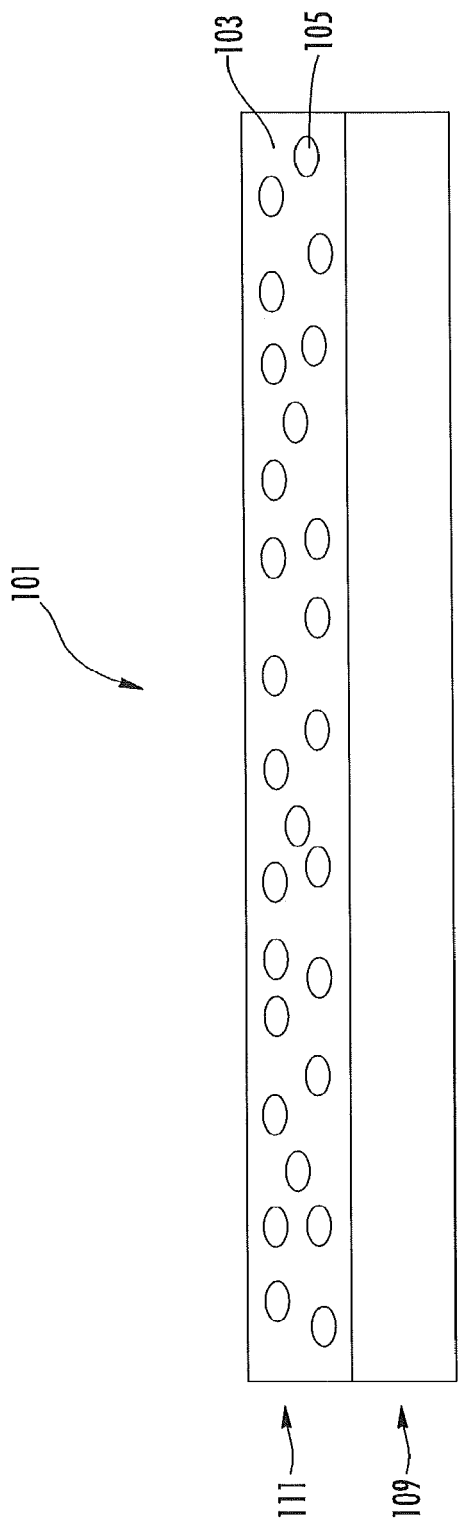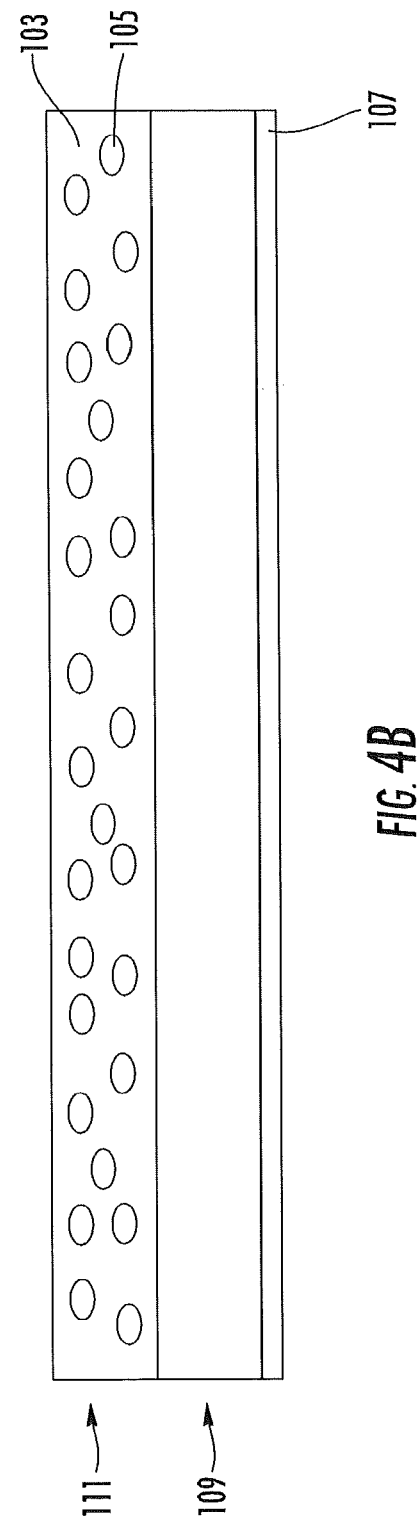

WOUND DRESSINGS, METHODS OF USING THE SAME AND METHODS OF FORMING THE SAME

CROSS-REFERENCE TO RELATED APPLICATIONS

The present application is a continuation of U.S. patent application Ser. No. 13/256,925, filed Oct. 4, 2011, which is a 35 U.S.C. § 371 national phase application of PCT International Application No. PCT/US2010/046209, having an international filing date of Aug. 20, 2010, and claiming priority to U.S. Provisional Application Ser. No. 61/235,927, filed Aug. 21, 2009, and U.S. Provisional Application Ser. No. 61/235,948, filed Aug. 21, 2009, the disclosures of each of which are hereby incorporated by reference herein in their entirety.

STATEMENT OF GOVERNMENT FUNDING

Research for this application was partially funded through a Phase I NIH SBIR grant entitled "Nitric Oxide-Releasing Antibacterial Wound Dressing" (grant number 5R43AI074098-02). The government may have certain rights to this application.

FIELD OF THE INVENTION

The present invention relates to materials that may be used as wound dressings that may release nitric oxide. The present invention also relates to methods of making and using wound dressings that may release nitric oxide.

BACKGROUND OF THE INVENTION

An important aspect for wound care is the control of infection, which may facilitate the healing process. Wound dressings are one of the most commonly used tools to protect the wound from infection. Antimicrobial agents are often incorporated into the wound dressing to treat and prevent infection. However, there are several disadvantages associated with use of antimicrobial agents. It has been observed that an increasing number of pathogens have developed resistance to the conventional antibiotic treatment. According to statistics, antibiotic-resistant pathogens are the primary reason for a majority of all lethal nosocomial infections. See Robson et al., Surg. Clin. N. Am. 77, 637-650 (1977). Furthermore, many antiseptic agents not only kill pathogens, but also impose a threat to the proliferating granulation tissue, fibroblasts and keratinocytes that may help with the wound healing process. Additionally, some antimicrobial agents may cause allergic reactions in some patients.

It is known that nitric oxide possesses a broad-spectrum of antimicrobial activity and may be used as an alternative to conventional antibiotics for drug resistant bacteria. Furthermore, some recent studies have demonstrated that nitric oxide may also play an important role in the wound healing process by promoting angiogenesis through stimulation of vascular endothelial growth factor (VEGF) and increased fibroblast collagen synthesis. See Schaffer M R, et al., *Diabetes-impaired healing and reduced wound nitric oxide synthesis: A possible pathophysiologic correlation.* Surgery 1997; 121(5):513-9; and Shi H P, et al., *The role of iNOS in wound healing.* Surgery 2001; 130 (2): 225-9. Thus, nitric oxide presents a promising addition and/or alternative to the conventional antibiotic treatment for wound care.

Nitric oxide is a gas at ambient temperature and atmospheric pressure, and it has a short half-life in a physiological milieu Several small molecule nitric oxide donor prodrugs have been developed which have contributed greatly to the understanding of nitric oxide in a number of disease states. However, due to issues with stability, indiscriminate NO-release, monotypical nitric oxide release kinetics, and inability to target specific tissue types no clinically viable solutions currently exist for administering nitric oxide outside of its gaseous form. Reproducibly delivering a the appropriate levels of nitric oxide for a given therapeutic indication is important because release of large amounts of nitric oxide may be toxic or create undesirable side effects such as decreases in angiogenesis or increased inflammation. Therefore, it has been challenging to use nitric oxide in the wound care field, other than via exogenous application, particularly in topical wound healing applications wherein nitric oxide has concentration dependent effects and benefits from delivery in a controlled and targeted manner.

Thus, the need exists for wound treatments and dressings that can release nitric oxide by a controlled delivery method.

SUMMARY OF THE INVENTION

Provided according to some embodiments of the invention are wound dressings that include a polymer matrix, and nitric oxide (NO)-releasing polysiloxane macromolecules within and/or on the polymer matrix. In some embodiments, such wound dressings are non-toxic and stably store NO. In some embodiments, the NO-releasing polysiloxane macromolecules include N-diazeniumdiolate functional groups and in some embodiments, include S-nitrosothiol functional groups.

In some embodiments of the invention, the concentration of the NO-releasing polysiloxane macromolecules is in a range of about 0.1 to about 20 weight percent.

The wound dressings may include additional additives. For example, the wound dressings may include a water-soluble porogen such as sodium chloride, sucrose, glucose, lactose, sorbitol, xylitol, polyethylene glycol, polyvinylpyrrollidone, polyvinyl alcohol and mixtures thereof. The wound dressings may also include at least one therapeutic agent such as antimicrobial compounds, anti-inflammatory agents, pain-relievers, immunosuppressants, vasodilators, wound healing agents, anti-biofilm agents and mixtures thereof.

In some embodiments, the wound dressing includes a polymer matrix that includes a hydrophilic polyurethane, such as, for example, an aliphatic polyether polyurethane that absorbs water in an amount ranging from 10 percent to 60 percent of its dry weight.

In some embodiments of the invention, the wound dressing includes a flexible, open-celled polyurethane foam that includes at least one polyisocyanate segment and at least one polyol segment. In some embodiments, the NO-releasing macromolecules are present within, and optionally crosslinked to, the polymer matrix of the polymer foam.

In some embodiments, the storage of nitric oxide in the wound dressing is in a range of 0.1 pmol NO $cm^{-2}$ to 100 pmol NO $cm^{-2}$, in some embodiments, in a range of 100 pmol NO $cm^{-2}$ to 1000 pmol NO $cm^{-2}$ and in some embodiments, in a range of 1 nmol NO $cm^{-2}$ to 10 µmol NO $cm^{-2}$.

In addition, provided according to some embodiments of the invention are wound dressing kits, methods of treating a wounds and methods of forming wound dressings.

BRIEF DESCRIPTION OF THE DRAWINGS

The accompanying drawings, which are included to provide a further understanding of the invention and are incorporated in and constitute a part of this application, illustrate certain embodiment(s) of the invention.

FIGS. 2A and 2B depict cross-sectional views of wound dressings according to embodiments of the invention.

FIGS. 4A and 4B depict cross-sectional views of wound dressings according to embodiments of the invention.

DETAILED DESCRIPTION OF EMBODIMENTS OF THE INVENTION

Figure 1:
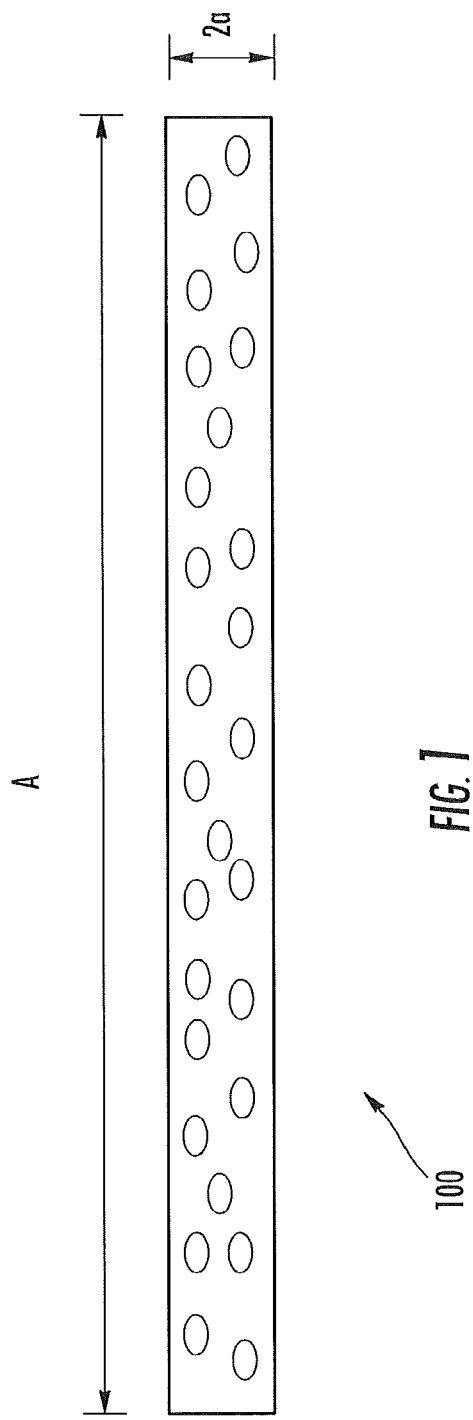
FIG. 1 depicts a cross-sectional view of a wound dressing according to an embodiment of the invention.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., NONO$^-$X$^+$).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO$^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group.

The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to Si(OR)$_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

Provided according to some embodiments of the invention are wound dressings that include a polymer matrix and nitric oxide (NO)-releasing polysiloxane macromolecules within and/or on the polymer matrix. The appropriate combination of polymer matrix and NO-releasing polysiloxane macromolecules may allow for a wound dressing that stably stores NO and may provide for controlled release of NO to the wound.

The Polymer Matrix

As used herein, the term "polymer matrix" is meant to encompass any natural or synthetic polymeric material that may retain at least some of the NO-releasing polysiloxane macromolecules therein or thereon. As such, the polymer matrix may be a homopolymer, heteropolymer, random copolymer, block copolymer, graft copolymer, mixture or blend of any suitable polymer(s), and it may be in any suitable physical form, such as a foam, film, woven or non-woven material, hydrogel, gel matrix, mixtures and blends thereof, and the like. As described in further detail below, the choice of polymeric matrix and its physico-chemical properties for a particular wound dressing may depend on factors such as the NO-releasing polysiloxane macromolecules within and/or on the polymer matrix, and the type of therapeutic action desired.

In some embodiments of the invention, the polymer matrix includes at least one of hydrophilic polyurethanes, hydrophilic polyacrylates, co-polymers of carboxymethyl-cellulose and acrylic acid, N-vinylpyrrolidone, poly(hydroxy acids), polyanhydrides, polyorthoesters, polyamides, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polylvinyl esters, polyvinyl halides (e.g., poly(vinyl chloride)), polyvinylpyrrolidone, polysiloxanes, poly(vinyl acetates), polystyrenes, polyurethane copolymers, cellulose, derivatized celluloses, alginates, poly(acrylic acid), poly(acrylic acid) derivatives, acrylic acid copolymers, methacrylic acid, methacrylic acid derivatives, methacrylic acid copolymers, poly(butyric acid), poly(val eric acid), poly(l actide-co-caprolactone), copolymers thereof and blends thereof.

In some embodiments of the invention, the polymer matrix may include a superabsorbent polymer (SAP). A polymer is considered superabsorbent, as defined per IUPAC, as a polymer that can absorb and retain large amounts of water relative to its own mass. SAPs may absorb water more than 500 times their own weight and may swell more than 1000 times their original volume. Exemplary SAPs include sodium polyacrylate, the polyurethane Tecophilic® TG-T2000, polyacrylamide copolymer, ethylene maleic anhydride copolymer, cross-linked carboxy-methyl-cellulose, polyvinyl alcohol copolymers, and cross-linked polyethylene oxide.

In some embodiments of the invention, polymers that are relatively hydrophobic, as defined by a water uptake value less than 10% by weight, may be used. Any suitable hydrophobic polymer may be used. However, exemplary polymers that are relatively hydrophobic include aromatic polyurethanes, silicone rubber, polycaprolactone, polycarbonate, polyvinylchloride, polyethylene, poly-L-lactide, poly-DL-glycolide, polyether etherketone (PEEK), polyamide, polyimide and polyvinyl acetate.

In addition, in some embodiments of the invention, the polymer matrix is modified to reduce swelling of the polymer and therefore prevent macromolecule leaching (e.g., NO-releasing polysiloxane macromolecule migration from the polymer matrix to the wound bed). Such modifications may include crosslinking of the polymer chains. The polymer matrix may also be modified by reacting the polymer with additional reagents. For example, the polymer may be modified to add hydrophilic groups, such as anionic, cationic and/or zwitterionic moeities, or to add hydrophobic groups such as silicone moeities, to the polymer chain.

In some embodiments, the polymer matrix includes polymer foam. The term "polymer foam" is meant to encompass any natural or synthetic polymer that is present as a foam and that may retain at least some NO-releasing polysiloxane macromolecules therein or thereon. In some embodiments, the polymer foam has an average cell size in a range of 50 μm and 600 μm. Furthermore, in some embodiments, the foam may be an open-celled foam. In some embodiments, the open cell walls of the foam may include pores of average size smaller than 100 μm, with the individual pore sizes between 10 and 80 As used herein, the term "open-celled foam" refers to a foam that has cells that are substantially interconnected, such as foams wherein at least 50%, at least 60%, at least 70%, at least 80%, or at least 90% of the cells are connected to at least one other cell. In some embodiments, the foam may be flexible. As used herein, the term "flexible" refers to foam that has a flexural strength of at least 40 MPa.

In some embodiments of the invention, the polymer foam is polyurethane foam. Any suitable polyurethane foam may be used. However, in some embodiments, the polyurethane foam may include at least one polyisocyanate segment and at least one polyol segment. Polyurethanes may be formed from the reaction of polyisocyanates and polyols. The polyisocyanate segment refers to a portion of the polyurethane formed from at least one polyisocyanate.

In some embodiments of the invention, the at least one polyisocyanate segment is formed from at least one of tolylene diisocyanate, methylphenylene diisocyanate, modified diisocyanates (e.g., uretdiones, isocyanurates, allophanates, biurets, isocyanate prepolymers and carbodiimide-modified isocyanates) and/or mixtures thereof. Exemplary diisocyanate include toluene diisocyanate; 1,4-tetramethylene diisocyanate; 1,4-hexamethylene diisocyanate; 1,6-hexamethylene diisocyanate; 1,12-dodecane diisocyante; cyclobutane-1,3-diisocyanate; cyclohexane-1,3-diisocyanate; cyclohexane-1,4-diisocyanate; 1-isocyanato-3,3,5-trimethyl-5-isocyanatomethyl cyclohexane; 2,4-hexahydrotolylene diisocyanate; 2,6-hexahydrotolylene diisocyanate; 2,6-hexahydro-1,3-phenylene diisocyanate; 2,6-hexahydro-1,4-phenylene diisocyanate; per-hydro-2,4'-diphenyl methane diisocyanate; per-hydro-4,4'-diphenyl methane diisocyanate; 1,3-phenylene diisocyanate; 1,4-phenylene diisocyanate; 2,4-tolylene diisocyanate, 2,6-toluene diisocyanates; diphenyl methane-2,4'-diisocyanate; diphenyl methane-4,4'-diisocyanate; naphthalene-1,5-diisocyanate; 1,3-xylylene diisocyanate; 1,4-xylylene diisocyanate; 4,4'-methylene-bis(cyclohexyl isocyanate); 4,4'-isopropyl-bis-(cyclohexyl isocyanate); 1,4-cyclohexyl diisocyanate; 3-isocyanatomethyl-3,5,5-trimethylcyclohexyl isocyanate (IPDI); 1-methyoxy-2,4-phenylene diisocyanate; 1-chloropyhenyl-2,4-diisocyante; p-(1-isocyanatoethyl)-phenyl isocyanate; m-(3-isocyanatobutyl)-phenyl isocyanate; 4-(2-isocyanate-cyclohexyl-methyl)-phenyl isocyanate; and mixtures thereof.

The polyol segment refers to a portion of the polyurethane foam formed from at least one polyol. The polyols may include polyether polyols and/or polyester polyols. Polyether polyols may have a significant amount of ether linkages in their structure, whereas the polyester polyols may have ester linkages within their structure. Any suitable polyol may be used. However, in some embodiments of the invention, the at least one polyol segment is formed from a diol having from 2 to 18 carbon atoms, and in some embodiments, a diol having 2 to 10 carbon atoms. Exemplary diols include 1,2-ethanediol, 1,3-propanediol, 1,4-butanediol, 1,6-hexanediol, 1,5-pentanediol, 1,10-decanediol, 2-methyl-1,3-propanediol, 2-methyl-2-butyl-1,3-propanediol, 2,2-dimethyl-1,3-propanediol, 2,2-dimethyl-1,4-butanediol, 2-ethyl-2-butyl-1,3-propanediol, neopentyl glycol hydroxypivalate, diethylene glycol and triethylene glycol. Triols and polyols of higher functionality may also be used and include compounds having 3 to 25, and in some embodiments, 3 to 18, and, in particular embodiments, 3 to 6 carbon atoms. Examples of triols which can be used are glycerol or trimethylolpropane. As polyols of higher functionality, it is possible, for example, to employ erythritol, pentaerythritol and sorbitol. In some embodiments, low molecular mass reaction products of the polyols may be used, for example, those of trimethylolpropane with alkylene oxides, such as ethylene oxide and/or propylene oxide. These low molecular mass polyols can be used individually or as mixtures.

Examples of polyether polyols include the commercially available polyols PETOL28-3B, PETOL36-3BR, and PETOL56-3 MB, Multranol®, Arcol® and Acclaim® (Bayer Material Science), and the Caradol® family of polyols (Shell Chemical Corporation).

Examples of polyester polyols that can be suitably used in the current invention include diethylene glycol adipate diol, dicaprylate diol, and in general, the esters of dicarboxylic and hydroxyl acids with glycol, and glycol functionalized polyester oligomers polylactate, polglycolate, polycaprylate, PET, and commercial formulations such as Desmophen® C polycarbonate diols and Desmophen® polyacrylate diols (Bayer).

In some embodiments, certain polyols or mixtures thereof specifically formulated for manufacture of high resiliency flexible polyurethane foams may be used. Examples of such polyols include a polyol having an ethylene oxide content in a range of 50% to 80%, a primary hydroxyl content of at least 40% and a molecular weight in a range of 2500 and 6000; a polymer polyol prepared by in situ polymerization of a high-functionality poly(oxyethylene)-poly(oxypropylene) oligomer, with a second poly(oxyethylene) polyol oligomer with a molecular weight ranging from 450 to 30,000 and an poly(oxyethylene) content greater than 70%; and biobased polyols derived from soybean oil, castor oil, palm oil, linseed oil and canola oil.

Other polyisocyanates and polyols may be used, including polyols and polyisocyanates having other functional groups therein. As such, in some embodiments, the polyisocyanates and polyols may include other functional groups such as ether, ester, urea, acrylate, pyrrolidone, vinyl, phenyl, and amino linkages, provided that the resulting polyurethane is suitable for forming a foam.

In some embodiments of the invention, the polymer foam includes a superabsorbent polymer (SAP). The superabsorbancy can be introduced in the foam structure by the inclusion of polymer segments that have superabsorbency in the polyol or the 'soft' segment of the foam. Examples of polymer segments having superabsorbency may include polyacrylamide copolymer, ethylene maleic anhydride copolymer, cross-linked carboxy-methyl-cellulose, polyvinyl alcohol copolymers, and cross-linked polyethylene oxide.

In some embodiments of the invention, polymer foams that are relatively hydrophobic may be used. Any suitable hydrophobic polymer may be used. Hydrophobicity can be introduced by selection of the polyisocyanate or the 'soft' segment of the polyurethane foam. Choosing highly hydrophobic polyisocyanates may results in a rigid foam, while lack of adequate hydrophobicity may prevent the formation of the foam structure.

Commonly used polyisocyanates for hydrophobic foams include diphenylmethane diisocyanate and its isomers, toluene diisocyanate, hexamethylene diisocyanate and mixtures thereof. In some embodiments, the polyisocyanates may also include copolymers of the diisocyanates previously mentioned. In some embodiments, the isocyanate groups may also be introduced at the termini of polymer segments of relatively hydrophobic polymers to provide a better control of the foam. Other polymers that are relatively hydrophobic include silicone rubber, polycaprolactone, polycarbonate, polyvinylchloride, polyethylene, poly-L-lactide, poly-DL-glycolide, polyetheretherketone (PEEK), polyamide, polyimide and polyvinyl acetate.

The polymer to be foamed may also be modified by reacting the polymer with additional reagents. For example, the polymer may be modified to add hydrophilic groups, such as anionic, cationic and/or zwitterionic moeities, or to add hydrophobic groups, such as silicone groups, to the polymer chain.

The polymer foam may be prepared by the reaction between the isocyanate moieties of the polyisocyanate 'hard' segments and the nucleophilic terminal groups of the polyols or 'soft' segments. The nucleophilic groups may include hydroxyl, amine and/or carboxylic groups.

In some embodiments, the foam may also contain chain extending segments in addition to the polyols and polyisocyanate building blocks. Polyamine co-reactants, due to the their reactivity with isocyanates, are the most commonly used chain extenders used to increase the chain length and flexibility of the foam. The most commonly used polyamines are polyaspartic esters, polyaldimines, butylenes diamines, and other short chain alkyl diamines.

Nitric Oxide-Releasing Polysiloxane Macromolecules

The term "NO-releasing polysiloxane macromolecules" refers to a structure synthesized from monomeric silane constituents that results in a larger molecular framework with a molar mass of at least 500 Da and a nominal diameter ranging from 0.1 nm-100 µm and may comprise the aggregation of two or more macromolecules, whereby the macromolecular structure is further modified with an NO donor group. For example, in some embodiments, the NO donor group may include diazeniumdiolate nitric oxide functional groups. In some embodiments, the NO donor group may include S-nitrosothiol functional groups.

In some embodiments of the invention, the NO-releasing polysiloxane macromolecules may be in the form of NO-releasing particles, such as those described in U.S. Publication No. 2009/0214618, the disclosure of which is incorporated by reference herein in its entirety. Such particles may be prepared by methods described therein.

As an example, in some embodiments of the invention, the NO-releasing particles include NO-loaded precipitated silica ranging from 20 nm to 10 μm in size. The NO-loaded precipitated silica may be formed from nitric oxide donor modified silane monomers into a co-condensed siloxane network. In some embodiments of the invention, the nitric oxide donor is an N-diazeniumdiolate.

In some embodiments of the invention, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method can be used to create co-condensed siloxane networks and materials more densely functionalized with NO-donors.

The co-condensed siloxane network can be silica particles with a uniformed size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In some embodiments, the alkoxysilane is a tetraalkoxysilane having the formula $Si(OR)_4$, wherein R is an alkyl group. The R groups can be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''-(NH-R')_n-Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane can be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino) propyl]trimethoxysilane (MAPS); N-butylaminopropyltrimethoxysilane (n-BAP3); t-butylaminopropyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: $NH[R'-Si(OR)_3]_2$, wherein R is alkyl and R' is alkylene. In some embodiments, the aminoalkoxysilane can be selected from bis(3-triethoxysilylpropyl)amine, bis-[3-(trimethoxysilyl)propyl]amine and bis-[(3-trimethoxysilyl) propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''-N(NONO^-X^+)-R'-Si(OR)_3$, wherein R is alkyl, R' is alkylene or aralkylene, R" is alkyl or alkylamine, and $X^+$ is a cation selected from the group consisting of $Na^+$, $K^+$ and $Li^+$.

In some embodiments of the invention, the co-condensed siloxane network further includes at least one crosslinkable functional moiety of formula $(R_1)_x(R_2)_y SiR_3$, wherein $R_1$ and $R_2$ is each independently $C_{1-5}$ alkyl or $C_{1-5}$ alkoxyl, X and Y is each independently 0, 1, 2, or 3, and X+Y equal to 3, and $R_3$ is a crosslinkable functional group. In a further embodiment, $R_1$ is $C_{1-3}$ alkoxyl, and $R_2$ is methyl. In another embodiment, $R_3$ is selected from the group consisting of acrylo, alkoxy, epoxy, hydroxy, mercapto, amino, isocyano, carboxy, vinyl and urea. $R_3$ imparts an additional functionality to the silica which results in a multifunctional device. Yet, in another embodiment, the crosslinkable functional moiety is selected from the group consisting of methacryloxymethyltrimethoxysilane, methacryloxypropyltrimethoxysilane, methacryloxypropyltriethoxysilane, 3-acryloxypropyl)trimethoxysilane, N-(3-methyacryloxy-2-hydroxypropyl)-3-aminopropyltriethoxysilane, 5,6-epoxyhexyltriethoxysilane, 2-(3,4-epoxycyclohexyl)ethyl trimethoxysilane, 3-glycidoxypropyl)trimethoxysilane, 3-aminopropyltrimethoxysilane, 3-aminopropyltriethoxysilane, 3-isocyanatopropyltriethoxysilane, 3-mercaptopropyltrimethoxysilane, mercaptopropyltriethoxysilane, 11-mercaptoundecyltrimethoxysilane, 2-cyanoethyltriethoxysilane, ureidopropyltriethoxysilane, ureidopropyltrimethoxysilane, vinylmethyldiethoxysilane, vinylmethyldimethoxysilane, vinyltriethoxysilane, vinyltrimethoxysilane, vinyltriisopropoxysilane and vinyltris(2-methoxyethoxy)silane. In some embodiments, $R_3$ may be used to cross-link the NO-donor modified silica with or within polymeric matrices.

The NO-releasing polysiloxane macromolecules may be present within and/or on the polymer matrix at any suitable concentration, but in some embodiments, the NO-releasing polysiloxane macromolecules are present within the polymer matrix at a concentration sufficient to increase the rate of wound healing, decrease inflammation and/or exert an antimicrobial effect. In particular embodiments, the concentration of the NO-releasing polysiloxane macromolecules may be in a range of about 0.1 to about 20 weight percent.

In some embodiments, the NO-releasing polysiloxane macromolecules may be uniformly distributed within the polymer matrix. Thus, in such embodiments, the concentration of NO-releasing polysiloxane macromolecules is substantially constant throughout the polymer matrix.

Interaction Between the Polymer Matrix and NO-Releasing Polysiloxane Macromolecules Wound healing occurs in several different phases, and may take place over 0-12 (or more) months. Wound healing phases include:
(i) Clotting
(ii) Cell Proliferation
(iii) Granulation Tissue Formation
(iv) Epithelialization
(v) Neovascularization or angiogenesis
(vi) Wound Contraction
(vii) Matrix deposition including collagen synthesis
(viii) Tissue Remodeling, including scar formation and scar remodeling The phase of wound healing plays a role in the selection of the NO-releasing polysiloxane macromolecules and the polymer matrix chosen. Nitric oxide may play a role in wound healing by a number of different mechanisms. First, extended exposure to low concentrations of nitric oxide may promote wound healing whereby nitric oxide acts as a signaling molecule in a number of wound healing cascades.

Additionally, nitric oxide may also play a role in mitigating inflammation following injury. Modulation of inflammatory cytokines and cells of the inflammatory response via nitric oxide may significantly alter the wound healing phases described above. Additionally, wound complications and pain may be significantly reduced with topical administration of nitric oxide as an anti-inflammatory agent. Furthermore, nitric oxide may act as a broad spectrum antimicrobial agent, particularly at relatively high concentrations. The antimicrobial effects of nitric oxide are broad ranging and different wound types may be colonized with different wound pathogens (e.g., gram negative bacteria, gram positive bacteria, fungi, etc.). Additionally, different pathogens may be more sensitive to nitric oxide than other pathogens. In some embodiments, nitric oxide may act as an antimicrobial agent by directly killing planktonic bacteria and other organisms; directly killing biofilm embedded bacteria and other organisms; indirectly killing microorganisms through nitrosative/oxidative stress; increasing drug permeability across microbial membranes; and/or preventing recurrence of infection or biofilm formation.

Therefore, in some embodiments, the nitric oxide released from a particular wound dressing may provide a particular therapeutic action, such as act as a signaling molecule in a wound healing cascade, act as an anti-inflammatory agent and/or act as an antimicrobial agent. The desired therapeutic action may determine which NO-releasing polysiloxane macromolecules and polymer matrix are used in a particular wound dressing. For example, two particular classes of nitric oxide donors are diazeniumdiolates and nitrosothiols. Both of these nitric oxide donors have at least one mechanism for the release of nitric oxide. Diazeniumdiolate may be triggered to release nitric oxide by exposure to water or another proton source, and an $O^2$-protected diazeniumdiolate may be triggered to release nitric oxide by exposure to light, enzymatic action and/or pH adjustment. Nitrosothiols may be triggered to release nitric oxide via thermal and radiative processes, and/or via interaction with copper and other thiols (e.g., glutathione). Therefore, the mechanism of release of nitric oxide from the NO-releasing polysiloxane macromolecules may affect which polymer matrix is chosen.

Specifically, because different NO-releasing polysiloxane macromolecules may release nitric oxide by different mechanisms, the polymer matrix chosen should complement the particular NO-releasing macromolecule employed. Several properties of the polymer matrix may be tailored based on the NO-releasing polysiloxane macromolecules used and the desired therapeutic action of the wound dressing. Such properties include:

(i) Moisture Uptake/Retention

The rate of moisture uptake may be tunable to meet the requirements of the NO-release kinetics of the macromolecule in order to achieve the desired therapeutic action of the wound dressing. The equilibrium moisture retention can vary from 5 percent for certain aliphatic polymers to over 2000 percent for hydrogels and superabsorbent polymers. Thus, in some embodiments, the polymer matrix has a low equilibrium moisture retention in a range of 0 to 10 percent. In some embodiments, the polymer matrix has a moderate equilibrium moisture retention in a range of 10 to 100 percent. Further, in some embodiments, the polymer matrix has a high equilibrium moisture retention of 100 percent or higher.

(ii) Moisture Vapor Transfer Rate (MVTR)

The MVTR may be tunable in breathable polymer films to match the requirements of a water reactive NO-releasing polysiloxane macromolecules in a thin film yet still maintain adequate MVTR for the desired wound or injury area. Wound dressings that maintain a moist wound bed are termed as occlusive. An optimum MVTR maintains a moist wound environment which activates debriding enzymes and growth factors that promote wound healing. Occlusive dressings also act as a barrier towards exogenous microbes, thereby preventing infection. Occlusive dressings are characterized by an MVTR of less than 35 g water/m$^2$/h (iii) Ability to Swell The ability of the wound dressing to swell without dissolution upon contact with wound moisture is beneficial in highly exudating wounds. The wound dressing serves to imbibe excess moisture that may otherwise cause wound maceration and foul odor.

(iv) Surface Energy

Hydrophobic wound dressings are characterized by low surface energy whereas charged and/or hydrophilic wound dressings have a high surface energy. Low surface energy is desirable to allow easy removal of the dressing without damaging the wound bed.

(v) Oxygen Permeability

Adequate oxygen level facilitates neovascularization, aids in collagen synthesis, and may prevent or minimize microbial infection of the wound. Due to damaged vasculature in wounds, there may be a low oxygen tension in the wound bed, leading to hypoxia and anaerobic metabolism that can delay the healing process. Wound dressings may be oxygen permeable so that the wound receives adequate topical oxygen for healing.

(vi) Nitric Oxide Permeability

The polymer matrix of the wound dressing may have adequate permeability towards nitric oxide such that the nitric oxide generated by the NO-releasing polysiloxane macromolecules is available to the wound bed at a desired therapeutic rate. Hydrophilic materials typically have a lower NO permeability towards nitric oxide as compared to hydrophobic materials. The NO permeability of the dressing may be matched to the release kinetics of the NO-releasing polysiloxane macromolecules and the rate of water uptake by the polymer, in order to provide for optimal release of NO from the dressing.

(vii) Biodegradability/Bioabsorbability

Biodegradability refers to the property of the wound dressing to break down into smaller molecular weight components under physiological conditions. Bioresorbability refers to the property by which the wound dressing can break down into smaller molecular weight segments and the segments are completely taken into the body without any biological reaction. This property is desirable if the dressing is to be used over a long-term for cavity-type wounds.

(viii) Tensile Strength

Tensile strength is the ability of the wound dressing to withstand breakage upon elongation in any direction. The wound dressing material needs to have adequate tensile strength in order to withstand stresses occurring as a result of normal patient wear.

(ix) Biocompatibility

The polymer matrix of the wound dressing may be biocompatible, non-toxic, and non-irritable.

(x) Ionic Character

The ionic character of the dressing may affect the dressing surface energy and biocompatibility. The ionic character of the dressing can be quantified by measurement of the zeta potential of the wound dressing material under physiological conditions. In some embodiments, the zeta potential of surfaces may be between −30 mV and +20 mV, and in some embodiments, between −10 mV and +10 mV, and in some embodiments, approximately zero. Surfaces with highly negative (<−30 mV) or highly positive (>+20 mV) zeta potential may be undesirable as they may have an anti- or pro-coagulant effect on the wound and may increase dressing surface energy.

(xi) Transparency

The ability of the wound dressing material to allow passage of visible light may allow for visual monitoring of the wound healing process. As used herein, a wound dressing or polymer matrix is transparent if it has an optical transparency value of 80 percent or more transmittance as measured via solid state spectrophotometry.

As moisture facilitates nitric oxide release from diazeniumdiolate-functionalized polysiloxane macromolecules, a wound dressing that includes diazeniumdiolate-modified polysiloxane macromolecules within and/or on a hydrophilic polymer will allow for the release of nitric oxide to a wound at a greater rate than would a hydrophobic polymer. Thus, the level of nitric oxide desired to be applied to the wound can be tailored by increasing or decreasing the hydrophilicity of the polymer. Therefore, by combining a hydrophilic polymer with a diazeniumdiolate-modified macromolecule, a concentrated dose of nitric oxide may be provided to a wound, and by combining a diazeniumdiolate-modified macromolecule with a relatively hydrophobic polymer, an "extended release" dose of nitric oxide may be provided to the wound. An extended release formulation may allow for release of nitric oxide over a predetermined time, such as 0-7 days. Additionally, as thermal and/or light energy may facilitate nitrosothiol modified polysiloxane macromolecule decomposition, the polymer matrix and/or additional layers above the polymer matrix including the nitrosothiol-modified polysiloxane macromolecules may be transparent so that light may facilitate nitric oxide release from the nitrosothiol. The transparency may be modified to control the level of nitric oxide release.

Thus, the polymer matrix and the NO-releasing polysiloxane macromolecules may be selected based on at least one property of the polymer matrix and at least one property of the NO-releasing polysiloxane macromolecules such that the interaction of the properties of the polymer matrix and the NO-releasing polysiloxane macromolecules provides a predetermined characteristic to the wound dressing. In some embodiments of the invention, the at least one property of the polymer matrix may include moisture uptake/retention, moisture vapor transfer rate (MVTR), surface energy, oxygen permeability, nitric oxide permeability, pore size biodegradability/bioabsorbability, tensile strength, biocompatibility, ionic character and/or transparency. In some embodiments of the invention, the at least one property of the NO-releasing polysiloxane macromolecules may include the nitric oxide release mechanism (e.g., water, heat, light, enzymatic, pH, and the like), total quantity of nitric oxide stored in moles NO/mg silica, the hydrophobicity/hydrophilicity of the co-condensed silica, and the biodegradability/bioresorbability of the macromolecular framework. The predetermined characteristic may be the ability of the nitric oxide in the wound dressing to signal one or more wound healing cascades, to act as an anti-inflammatory agent and/or to act as an antimicrobial agent.

As used herein, the term "interaction of the properties" refers to the ability of particular properties of the polymer matrix and particular properties to the NO-releasing polysiloxane macromolecules to combine to produce a wound dressing that has a predetermined characteristic, as defined herein. For example, the particular hydrophilicity of the polymer matrix may interact with a particular concentration of water reactive NO-releasing polysiloxane macromolecules to produce the desired release rate of nitric oxide from the polymer matrix.

An exemplary calculation of the reaction rate of the nitric oxide release as a function of the rate of a dressing's water uptake, is shown below. In this calculation, the absorption of water over time in the wound dressing is modeled. It is assumed that the release of NO from the NO-releasing polysiloxane macromolecules commences immediately upon contact with the diffused water.

Referring to FIG. 1, for a thin film 100 (of thickness 2a) of a polymer matrix including uniformly dispersed NO-releasing polysiloxane macromolecules at a percent loading concentration of G (100×g NO-releasing silica/g polymer), when the film is immersed in water, water diffuses into the film at a rate given by the unsteady state diffusion expression:

$$\frac{C(t)}{C_\infty} = \left(\frac{8}{\pi^2}\right)e^{-\frac{Dt\pi^2}{4a^2}}$$

wherein D=diffusion coefficient of water in the polymer matrix, C(t)=concentration of water at time t, and $C_\infty$ is the concentration of water at equilibrium, which is the surrounding concentration (55 M). In a given time, t, the water diffuses only up to a certain thickness into the polymer film, thereby 'activating' the NO-releasing polysiloxane macromolecules up to that depth, z(t). The concentration of water in the film is the concentration of water only up to this depth and is equal to the mass of water diffused up to that depth, divided by volume of the penetration, thus $$C(t) = \frac{m_{water}(t)}{Az(t)\varepsilon}$$

where $\varepsilon$ is the porosity of the polymer film, which is considered because the water will only penetrate into the interconnecting pores between the polymer chains. The mass of water in the film at given time (t) can be calculated by measuring the rate of water uptake (U) by the bulk polymer, which can be determined experimentally, and is defined as:

$$U(t) = \frac{100 \times m_{water}}{M_{poly}}$$

where $M_{poly}$=mass of the polymer film. Thus substituting this expression for the mass of water, in the expression for depth of penetration as defined above, $$z(t) = \frac{0.01 U(t) M_{poly}}{A\varepsilon C_\infty}$$

$$z(t) = \frac{0.01 U(t) M_{poly}}{A\varepsilon C_\infty}\left(\frac{\pi^2}{8}\right)e^{Dt\frac{\pi^2}{4a^2}}.$$

If the intrinsic rate of NO release of the NO-releasing polysiloxane macromolecules is known as a function of time, f(t), the rate of NO release from the silica in the polymer that have been 'activated' at time t is given by:

$$NO(t) = m_{NO}(t) \times f(t)$$

Where [NO(t)]=micromoles of NO released at time t, $m_{NO}$=mass of NO-releasing silica activated at time (t). By definition the NO-releasing co-condensed silica loading in the polymer wound dressing is expressed as, $$G = \frac{100 \times m_{NO}}{M_{poly}}$$

where $M_{poly}$=mass of the entire polymer film, of which only $M_{poly}(t)$ has been 'wet' by the water at time (t). Therefore, $$m_{NO}(t) = 0.01 G M_{poly}(t)$$

$$m_{NO}(t) = 0.01 G A \rho_{poly} z(t)$$

and hence, $$NO(t) = 0.01 G A \rho_{poly} \times \frac{0.01 U(t) M_{poly}}{A \varepsilon C_\infty} \left(\frac{\pi^2}{8}\right) e^{Dt\frac{\pi^2}{4a^2}}$$

Therefore, the overall rate of NO release from the polymer is given by $$NO(t) = 10^{-4} \frac{GU(t)}{\varepsilon C_\infty} \rho_{poly} M_{poly} \left(\frac{\pi^2}{8}\right) f(t) e^{\frac{D t \pi^2}{4 a^2}}.$$

In some embodiments of the invention, the storage of nitric oxide in the dressing is in a range of 0.1 pmol NO cm$^{-2}$ to 100 pmol NO cm$^{-2}$. In some embodiments, the storage of nitric oxide release in the dressing is in a range of 10 pmol NO cm$^{-2}$ to 1 nmol NO cm$^{-2}$. In some embodiments, the storage of nitric oxide in the dressing is in a range of 1 nmol NO cm$^{-2}$ to 10 µmol NO cm$^{-2}$. Total nitric oxide storage (t[NO]) and surface flux can be measured in real-time via the chemiluminescent detection of nitric oxide reviewed by Hetrick et al. (Hetrick et al. *Analytical Chemistry of Nitric Oxide, Annu. Rev. Anal. Chem.* 2009, 2, 409-433, which is hereby incorporated by reference in its entirety). Additional kinetic parameters for nitric oxide release that can be measured during this technique are the time to release the maximum flux of NO ($t_m$), quantity of NO at the maximum flux ([NO]$_m$), half-life of nitric oxide release ($t_{1/2}$), and nitric oxide release duration ($t_d$).

In some embodiments of the invention, the instantaneous flux of nitric oxide release from the hydrated dressing surface is in a range of 0.1 pmol NO cm$^{-2}$ s$^{-1}$ to 100 pmol NO cm$^{-2}$ s$^{-1}$ and constitutes a slow initial rate of release. In some embodiments, the instantaneous flux of nitric oxide release from the hydrated dressing surface is in a range of 100 pmol NO cm$^{-2}$ s$^{-1}$ to 1000 pmol NO cm$^{-2}$ s$^{-1}$ and constitutes an intermediate rate of release. In some embodiments, the instantaneous flux of nitric oxide from the hydrated dressing surface is in a range of 1 nmol NO cm$^{-2}$ s$^{-1}$ to 10 µmol NO cm$^{-2}$ s$^{-1}$ and constitutes a rapid burst or fast NO-release kinetics.

Stability

According to some embodiments of the invention, the wound dressings can stably store the NO so that NO is not released prior to its intended therapeutic use. In some embodiments, 95 percent or more of the original NO loading is retained after one week at 25° C. Furthermore, in some embodiments, 85 percent of the NO loading is retained up to 2 years at 25° C.

In some embodiments of the invention, the wound dressings form a stable matrix whereby the leaching of silica particles is minimized. The thermodynamics of particulate leaching from polymeric matrices has not been a challenge previously encountered in the prior art. Leaching of siloxane based macromolecules can be determined via static light scattering or elemental analysis for Si in the soak solutions. In some embodiments, greater than 98 percent of the embedded NO-releasing polysiloxane macromolecules is retained following incubation under physiological conditions (pH=7.4, 37° C., phosphate buffered saline) for 48 hours. In other embodiments, greater than 95 percent of the embedded NO-releasing polysiloxane macromolecules is retained following incubation under physiological conditions (pH=7.4, 37° C., phosphate buffered saline) for greater than 30 days.

Example Embodiments

In some embodiments, the NO-releasing polysiloxane macromolecule is Nitricil™ (Novan, Inc.), which is a diazeniumdiolate-modified precipitated silica.

In some embodiments, the polymer matrix is an aliphatic polyether polyurethane that absorbs water in an amount of about 6 percent to about 100 percent of its dry weight. In some embodiments, the aliphatic polyether polyurethane absorbs water in an amount of about 10 to 60 percent of its dry weight, and in some embodiments, 10 to 20 percent of its dry weight.

In some embodiments, the polymer matrix is a superabsorbent polymer that absorbs water in an amount of at least 100 percent and ranging up to 5000 percent of its dry weight. In some embodiments, the polymer matrix includes Tecophilic® Aliphatic thermoplastic polyurethane from Lubrizol, Inc.

Additives

In addition to the NO-releasing polysiloxane macromolecules, other additives may be present within and/or on the polymer matrix. Such additives may alter the properties of the polymeric matrix. For example, in some embodiments, the wound dressing may further include a water-soluble porogen. The water-soluble porogen is an additive that may facilitate water uptake and diffusion in the polymer matrix. Any suitable porogen may be used, but in some embodiments, the porogen may include sodium chloride, sucrose, glucose, lactose, sorbitol, xylitol, polyethylene glycol, polyvinylpyrrollidone, polyvinyl alcohol and mixtures thereof.

The properties of the polymer matrix and water uptake may also affect the release of nitric oxide, and so additives that affect the properties of the polymer matrix and/or water uptake may in turn affect the rate of release of nitric oxide from the NO-releasing polysiloxane macromolecules.

Additives may also be included in the polymer foam that directly affect the release of nitric oxide from the NO-releasing macromolecules. For example, in some embodiments, basic or other anionic species may be used to buffer the pH of the polymer foam to slow diazeniumdiolate decomposition and resulting nitric oxide release. In other embodiments, chelating agents may be used to scavenge metal ions like $Fe^{2+}$, $Cu^{2+}$ and $Cu^+$ to preserve nitrosothiol NO donor stability and prevent rapid nitric oxide release. In some embodiments, additives may be added to enhance NO donor decomposition given the inherently slow NO-release kinetics of the NO-releasing polysiloxane macromolecule. For example, acidic or carboxylic acid functionalized additives may be added to the foam to create a low internal foam pH upon hydration and accelerate the decomposition of N-diazeniumdiolate donors. In another embodiment, cysteine or glutathione may be impregnated into the foam matrix to facilitate transnitrosation and subsequent thiol mediated decomposition of nitrosothiol containing macromolecules.

In addition, other additives useful for foam formation and processing may be included. For example, surface-active agents may be added to enhance mixing, act as mold-release agents and/or to influence the final cellular structure of the foam. Furthermore, blowing agents, and byproducts therefrom, may also be present within the polymer foam. Blowing agents are described in further detail below. Additives that may be useful in forming foams include surface-active agents to enhance mixing as well as to influence the final foam structure, and mold-release agents. Examplary surface active agents may be found in U.S. Pat. No. 6,316,662, the disclosure of which is incorporated herein in its entirety.

Additives may be present in the polymer matrix that may act to provide additional therapeutic effects to the wound dressing, either acting synergistically or separately from the NO-releasing polysiloxane macromolecules. For example, in some embodiments, the wound dressings may also include at least one therapeutic agent such as antimicrobial agents, anti-inflammatory agents, analgesic agents, anesthetic agents, antihistamine agents, antiseptic agents, immunosuppressants, antihemorrhagic agents, vasodilators, wound healing agents, anti-biofilm agents and mixtures thereof.

Examples of antimicrobial agents include penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenem, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil. Examples of antihistamine agents include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include thrombin, phytonadione, protamine sulfate, aminocaproic acid, tranexamic acid, carbazochrome, carbaxochrome sodium sulfanate, rutin and hesperidin.

Wound Dressing Devices

Figure 3A:
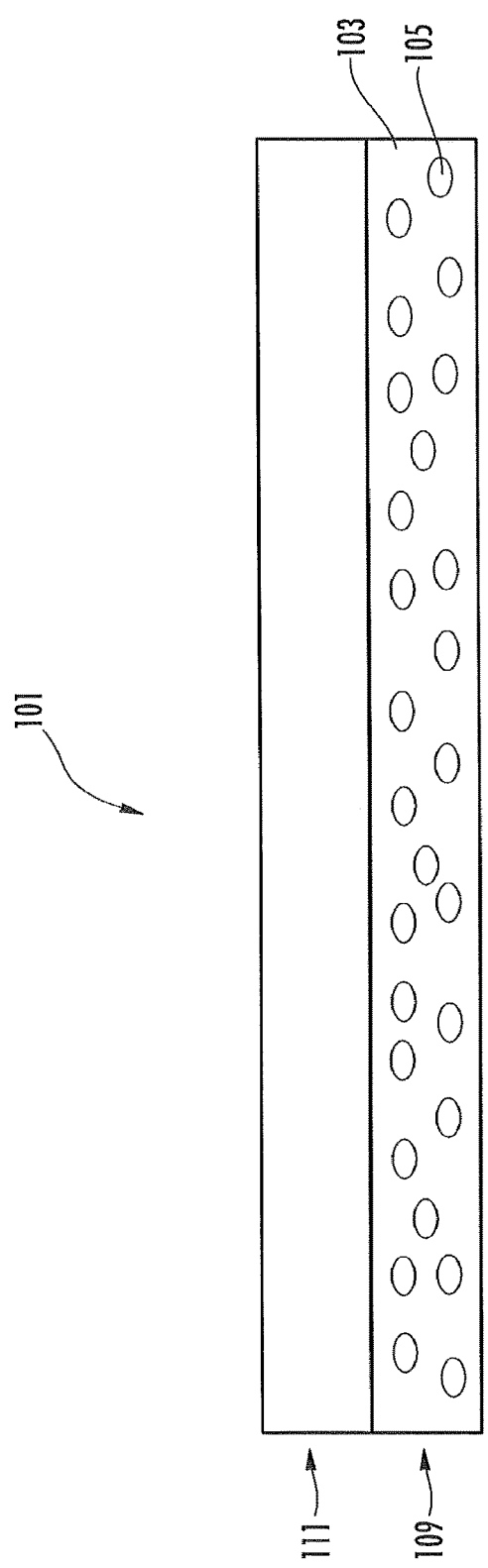
FIGS. 3A and 3B depict cross-sectional views of wound dressings according to embodiments of the invention.
Figure 3B:
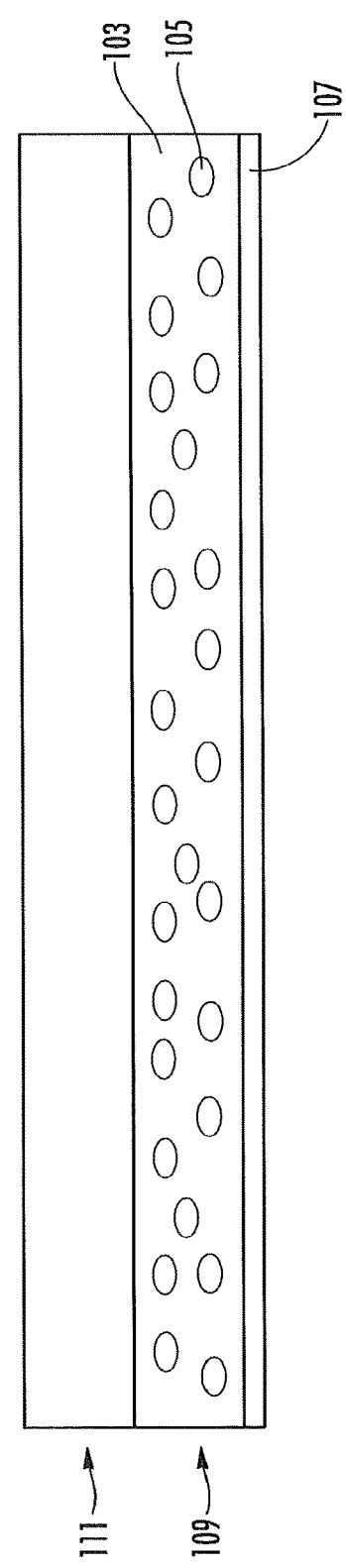

Any suitable configuration of wound dressing device may be used. Referring to FIG. 2A, in some embodiments, the wound dressing 101 is a single layer that includes a polymer matrix 103 and NO-releasing polysiloxane macromolecules 105 therein and/or thereon. Referring to FIG. 2B, in some embodiments, the single layer wound dressing may include a medical-grade adhesive 107 on the surface of the wound dressing that contacts the wound bed. Referring to FIGS. 3-5, in some embodiments, the wound dressing may include two or more layers. For example, referring to FIG. 3A, in some embodiments, the wound dressing 101 has two layers, a first layer 109 that includes a polymer matrix 103 and NO-releasing polysiloxane macromolecules 105 within and/or on the polymer matrix 103; and a second layer 111 on the first layer 109. Furthermore, referring to FIG. 3B, in some embodiments, a medical-grade adhesive 107 may be on the surface of the first layer 109 that contacts the wound bed. Referring to FIG. 4A, in some embodiments, the polymer matrix 103 and NO-releasing polysiloxane macromolecules 105 within and/or on the polymer matrix 103 is included in the second layer 111, which may provide an anti-microbial barrier to the wound dressing 101. Thus, the first layer 109 may or may not include a polymer matrix 103 and NO-releasing polysiloxane macromolecules 105 within and/or on the polymer matrix 103. Regardless of whether the first layer 109 includes a polymer matrix 103 and NO-releasing polysiloxane macromolecules 105 within and/or on the polymer matrix 103, a medical-grade adhesive 107 may be on the surface of the first layer 109 that contacts the wound bed. Additionally, in some embodiments, the first layer 109 or second layer 111 may be substantially free of NO-releasing polysiloxane macromolecules 105.

Figure 5A:
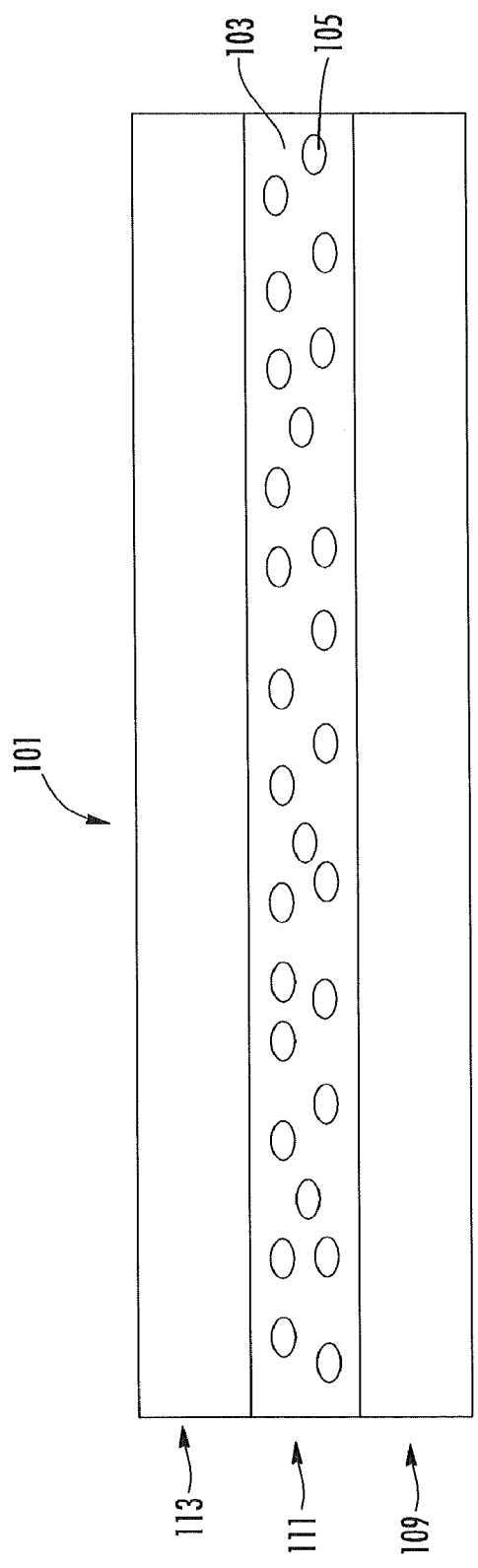
FIGS. 5A and 5B depict cross-sectional views of wound dressings according to embodiments of the invention.
Figure 5B:
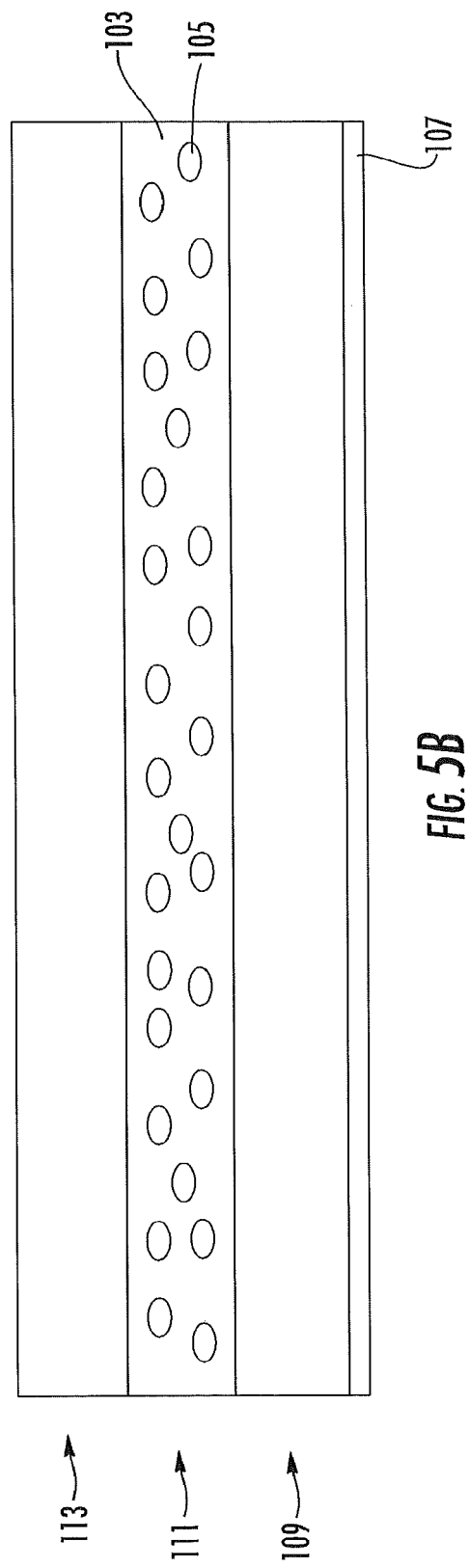

Referring to FIGS. 5A and 5B, as another example, in some embodiments, the wound dressing 101 has three layers, a first layer 109 that contacts the wound bed, a second layer 111 on the first layer 109, and a third layer 113 on the second layer 111. A medical-grade adhesive 107 may be on the surface of the first layer 109 (FIG. 5B). The polymer matrix 103 and NO-releasing polysiloxane macromolecules 105 within and/or on the polymer matrix 103 may be present in the first layer 109, the second layer 111 and/or the third layer 113. In some embodiments, at least one of the first layer 109, the second layer 111 and the third layer 113 is substantially free of NO-releasing polysiloxane macromolecules 105. However, as shown in FIG. 5, in some embodiments, the polymer matrix 103 and NO-releasing polysiloxane macromolecules 105 within and/or on the polymer matrix 103 are present only in the second layer 111. The first layer 109 may act as a wound contact layer that prevents NO-releasing polysiloxane macromolecules 105 from leaching into the wound and/or provides a hydrophobic or nonstick wound contact surface. The third layer 113 may act to contain nitric oxide within the wound dressing 101 and may control the MVTR, oxygen diffusion and/or microbial penetration into the wound dressing 101.

Figure 6A:
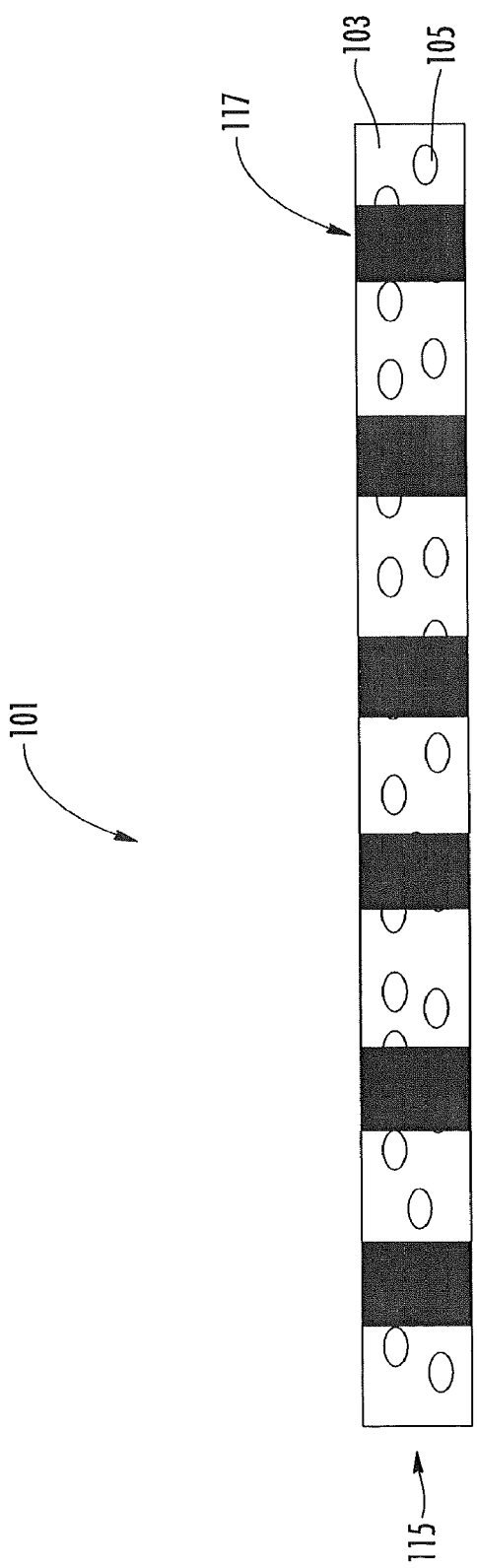
FIGS. 6A and 6B depict cross-sectional views of wound dressings according to embodiments of the invention.
Figure 6B:
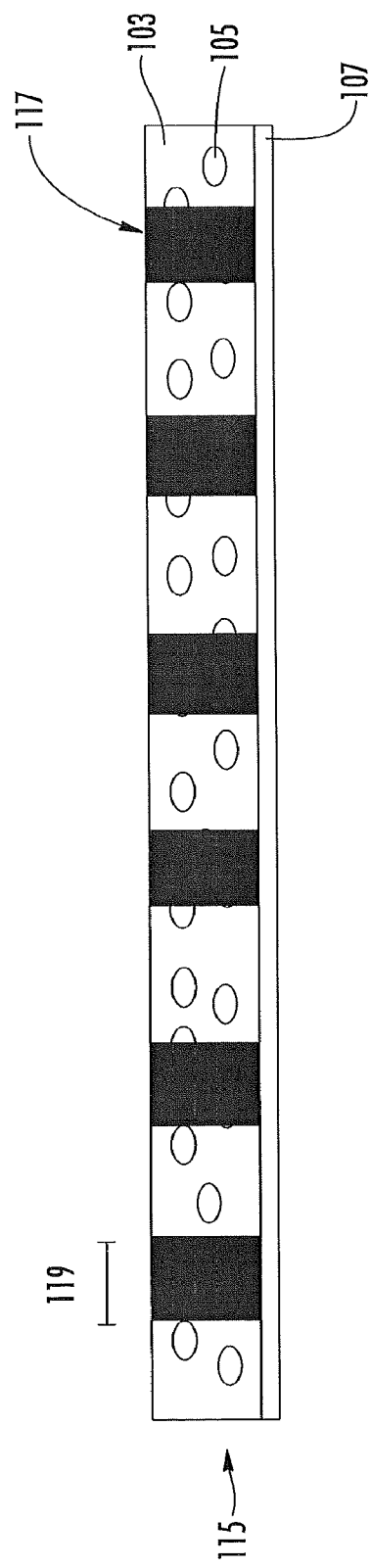

Referring to FIG. 6A, in some embodiments, at least one layer of the wound dressing 101 includes a perforated layer 115. A "perforated layer" 115 includes at least one hole 117 defined within polymer matrix 103. In some embodiments, the polymer matrix 103 includes an array of holes 117 defined therein. The holes 117 in the polymer matrix 103 may have any suitable width 119, but in some embodiments, the holes 117 have a width 119 in a range of about 200 to about 5000 microns. The term "width" 119 refers to the largest distance across the hole. For a cylindrical hole 117, the width 119 is the diameter. The width 119 of the holes 117 may be chosen based on a variety of parameters, such as moisture of the wound, polymer matrix, thickness of the layer and/or dressing, whether adhesive is used and/or whether it is being used with negative pressure wound therapy (NPWT). In some embodiments, the NO-releasing polysiloxane macromolecules 105 may be present in the polymer matrix 103 of the perforated layer 115. Such perforated layers 115 may be used with other perforated layers 115 and/or with non-perforated layers, in any suitable combination. Additionally, the perforated layers 115 may not include NO-releasing polysiloxane macromolecules 105 and/or may be used in combination with other layers that include a polymer matrix 103 and NO-releasing polysiloxane macromolecules 105 within and/or on the polymer matrix 103. Furthermore, as shown in FIG. 6B, a medical-grade adhesive 107 may be on the surface of the perforated layer 115 that contacts the wound bed. The use of a perforated layer 115 may allow for moisture from the wound to interact with NO-releasing silica in a layer on the perforated layer 115, may increase gas (e.g., nitric oxide) diffusion to the wound bed, and provide a suitable material for use with NPWT.

The perforated layer 115 may be formed by any suitable method. However, in some embodiments, the perforated layer 115 is formed by using a mold, or by pressing an object into the polymer matrix 103 to form at least one hole 117, wherein the hole edges may also be melted and fused depending on the nature of the polymer matrix 103. Additionally, in some embodiments, the holes 117 of the perforated layers 115 may be formed by curing the polymer matrix 103 in a mold, e.g., in an anhydrous and/or low temperature process, and then peeled out or packaged in individual perforated trays.

According to some embodiments of the invention, additional therapeutic agents, such as those described herein, may be present in any of the layers of the wound dressing. As an example, in some embodiments, a layer that is substantially free of NO-releasing polysiloxane macromolecules may include at least one therapeutic agent. As an additional example, a layer that includes NO-releasing polysiloxane macromolecules may also include at least one additional therapeutic agent.

In some embodiments, the wound dressing may further include a polymer backing layer that contacts the polymer matrix or a polymer layer on the polymer matrix. In some embodiments, the wound dressing is an island wound dressing, and the polymer backing layer, and optionally at least a portion of the polymer matrix that contacts the wound bed, may include a medical grade adhesive thereon. For example, the wound dressing may include a polymer backing layer and a polymer matrix layer including a polymer matrix having NO-releasing polysiloxane macromolecules therein or thereon, wherein the polymer matrix layer is attached to a portion of the polymer backing layer, and wherein at least a portion of the polymer backing layer that is facing but not attached to the polymer matrix layer is coated with a medical grade adhesive. Such wound dressings may also include additional layers, such as a wound contact layer, wherein the wound contact layer is on the face of the polymer matrix layer that is not attached to the polymer backing layer.

Each layer of wound dressing according to embodiments of the invention may have any suitable thickness. However, in some embodiments, one or more layers of the wound dressing may have a thickness in a range of about 10 to about 5000 microns. In some embodiments of the invention, at least one layer of the wound dressing may be substantially transparent. Further, in some embodiments, the wound dressing as a whole may be substantially transparent. The term "substantially transparent" refers to a material that has a percent transmittance of 80 percent or more, as determined using a solid state spectrophotometer. Additionally, as described above, in some embodiments, at least one layer of the wound dressing has a medical-grade adhesive thereon. For example, the surface of the wound dressing that contacts the wound may have a medical-grade adhesive thereon.

Examples of medical grade adhesives that can be safely used on skin are acrylate-based adhesives, such as 2-ethylhexyl acrylate, isooctyl acrylate or n-butyl acrylate copolymerized with polar functional monomers such as acrylic acid, methacrylic acid, vinyl acetate, methyl acrylate, N-vinylcaprolactam, or hydroxyethyl methacrylate. Additional examples include octylcyanoacrylate, AcrySure™ adhesives (MACtac), adhesives based on silk protein, silicone gel based adhesives (Silbione® by Bluestar Silicones) and polyurethane based adhesive blends.

Wound Dressing Kits

As described above, wound healing may be effected through prolonged low concentrations of nitric oxide administration whereby nitric oxide acts as a signaling molecule in a number of wound healing cascades. In some embodiments, the instantaneous flux of nitric oxide release from hydrated dressing surface necessary to promote wound healing may be in the range of 0.5 pmol NO $cm^{-2}$ $s^{-1}$ to 20 pmol NO $cm^{-2}$ $s^{-1}$ upon initial application to the patient and constitutes a slow rate of release. An intermediate NO-releasing wound dressing may mitigate the inflammatory phase immediately following injury, following debridement of a chronic wound, in stalled wounds, or in infected wounds. In the inflammatory phase, the flux of nitric oxide released from the hydrated dressing surface is in a range of 20 pmol NO $cm^{-2}$ $s^{-1}$ to 1000 pmol NO $cm^{-2}$ $s^{-1}$ upon initial application to the patient and constitutes an intermediate rate of release. High levels of NO-released from a third matrix/NO-releasing polysiloxane macromolecule composition may be necessary to effect antimicrobial activity, using the rapid burst of nitric oxide to kill microorganisms through oxidative/nitrosative intermediates. In these embodiments, the flux of nitric oxide released from the hydrated dressing surface is in a range of 1 nmol NO $cm^{-2}$ $s^{-1}$ to 1 µmol NO $cm^{-2}$ $s^{-1}$ upon initial application and may constitute the rapid burst of nitric oxide necessary to provide a one or more log reduction against a broad range of microorganisms.

Therefore, provided according to some embodiments of the invention are kits that include wound dressings directed to a course of therapy with three unique dressing types of compositions designed to target these three wound processes. For a particular wound, a regiment may be implemented for a specified number of days whereby the three unique dressings are administered in sequence or repeated at some frequency (e.g., to keep microbial burden low).

Methods of Treating a Wound

In some embodiments of the invention, provided are methods of treating a wound by applying a wound dressing according to an embodiment of the invention. Such methods may be used in combination with any other known methods of wound treatment, including the application of medicaments, such as those that have anti-inflammatory, pain-relieving, immunosuppressant, vasodilating, wound healing and/or anti-biofilm forming properties. For the methods used herein, additional therapeutic agents and methods may be used prior to, concurrently with or after application with a gel according to embodiments of the invention. Wound dressings according to embodiments of the invention may also be used in combination with other wound dressings known to those of skill in the art.

In some embodiments of the invention, the wound dressings provided herein may be used in conjunction with at least one agent that can disrupt biofilm macrostructure prior to or in conjunction with the application of the wound dressing. In some embodiments, the anti-biofilm agent may disrupt the extracellular matrix of the biofilm. Examples of anti-biofilm agents that may act in this manner include lactoferrin, periodate, xylitol, DNase, protease, and an enzyme that degrades extracellular polysaccharides. In some embodiments of the invention, the formulation of the anti-biofilm agent may be acidic to promote enzyme activity of the DNase (e.g., mammalian DNases such as DNase II) and the acidic conditions simultaneously may also enhance the rate NO release from diazeniumdiolate modified silica. In some embodiments, the protease may include at least one of proteinase K, trypsin, Pectinex Ultra SP (PUS) and pancreatin. In some embodiments, enzymes that degrade extracellular polysaccharides may include N-acetylglucosaminidases (e.g., dispersin B).

In some embodiments of the invention, the anti-biofilm agent may act by affecting the transcriptional, translational and/or post-translational regulation of quorum-sensing genes or gene products in the infecting organism(s). For example, the anti-biofilm agents may include at least one of hamamelitannin, cyclic di-GMP and sublethal concentrations of nitric oxide.

The anti-biofilm agents may also act by other mechanisms. For example, the anti-biofilm agent may cause the infecting organism to transition from a sessile state to a metabolically active state. As another example, the anti-biofilm agent may act by causing the infecting organism(s) to transition from a non-motile state to a motile phenotype.

In some embodiments of the invention, the wound dressings provided herein may be used in conjunction with a wound debridement procedure. For example, in some embodiments, wounds may first be treated with a debridement procedure; and then a wound dressing according to an embodiment of the invention may be applied to the debrided wound. The wound dressings according to embodiments of the invention may increase the rate of wound healing, decrease inflammation and/or exert an antimicrobial effect. The wound dressings according to embodiments of the invention may be used in conjunction with any suitable debridement procedure. For example, the debridement procedure may be selective or nonselective.

In some embodiments, the debridement procedure may include at least one of surgical, enzymatic, autolytic, sharp, mechanical and biological processes. Any suitable surgical method may be used, but in some embodiments, the surgical method may involve a surgeon cutting away nonviable tissue in the wound. Any suitable enzymatic method may be used, but in some embodiments, the enzymatic method may involve the use of one or more proteases, their required cofactors, and optionally any enhancing agents, to digest the nonviable tissue in the wound. Exemplary proteases include trypsin, papain or other vegetable-derived proteases and collagenase. Any suitable autolytic method may be used, but in some embodiments, the autolytic method may involve maintaining a moist wound environment in order to promote the breakdown of nonviable tissue by enzymes that are naturally produced by the body. Any suitable mechanical method may be used, but in some embodiments, the mechanical methods may include wet-to-dry gauze, irrigation, pulsatile lavage, whirlpool therapy and/or low frequency ultrasound. Any suitable sharp method may be used, but in some embodiments, the sharp method may involve cutting away nonviable tissue by qualified clinical staff (e.g. RN or nurse practitioner). Any suitable biological method may be used, but in some embodiments, the biological method may involve the use of maggots, which selectively digest the nonviable tissue in the wound. These debridement methods may be used alone or in combination.

After the wound is debrided, a wound dressing according to an embodiment of the invention may be applied. Additional processes may be performed and therapeutic agents may be applied. For example, after wound debridement, an anti-biofilm agent may be applied to the wound prior to or in conjunction with the application of the wound dressing. Exemplary anti-biofilm agents include acetylsalicylic acid (aspirin), cyclic di-GMP, lactoferrin, gallium, selenium, as described above. Other compounds, such as hamamelitannin (witch hazel extract), arginine and c-di-GMP, may also be applied.

Also provided according to some embodiments of the invention are methods of using a wound dressing according to an embodiment of the invention in conjuction with negative pressure wound therapy (NPWT).

Subjects suitable to be treated with wound dressings or methods according to an embodiments of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

Methods of Forming Wound Dressings

The wound dressings described herein may be formed by any suitable method. However, provided according to some embodiments of the invention are methods of forming wound dressings. In some embodiments, incorporation of NO-releasing polysiloxane macromolecules can be achieved through physically embedding the particles into polymer surfaces, via electrostatic association of particles onto polymeric surfaces, and/or by covalent attachment or cross-linking of particles onto reactive groups on the surface of a polymer, within the polymer and/or within cells of a foam. In some embodiments, methods of forming wound dressings include combining NO-releasing polysiloxane macromolecules and at least one monomer; and polymerizing the at least one monomer to form a polymer matrix comprising the NO-releasing polysiloxane macromolecules. The monomer may be polymerized by any suitable method, but in some embodiments, the monomer is polymerized by photocuring and/or moisture curing, with or without an initiator. In some embodiments, the monomer may be polymerized upon contact with the wound environment, e.g., via the moisture in the wound. In some embodiments, a single layer wound dressing may be formed by a method that includes solvent casting a solution of polymer and NO-releasing polysiloxane macromolecules.

In some embodiments, the polymerization occurs via liquid casting or molten polymer extrusion. In some embodiments, a liquid monomer, NO-releasing polysiloxane macromolecules and an initiator are deposited on a surface and polymerization proceeds upon activation of the initiator. Polymerizable groups can also be used to functionalize the exterior of the particles, whereupon, the particles can be co-polymerized into a polymer during the polymerization process.

In some embodiments of the invention, methods of forming the wound dressings include dispersing the NO-releasing polysiloxane macromolecules in a mixture of foam forming monomers; polymerizing the foam forming monomers to form a polymer; and then foaming the polymer.

In some embodiments, methods of forming wound dressings include reacting functional groups on the NO-releasing polysiloxane macromolecules with at least one foam forming monomer; polymerizing the at least one foam forming monomer to form a polymer including the NO-releasing polysiloxane macromolecules therein; and then foaming the polymer.

In some embodiments, polyurethane foam dressings may be prepared by the reaction of polyols with polyisocyanates added in stoichiometric excess, with other co-reactants added as required. In conventional foam manufacture, a stoichiometric amount of water is added to the reactant mix. The water may react with the isocyanate groups to form $CO_2$ which bubbles through the polymerizing mass, creating a cellular structure of flexible foams.

For water reactive NO-releasing polysiloxane macromolecules, water may not be used in the preparation of NO-releasing foam dressings as water may activate the NO-releasing polysiloxane macromolecules, resulting in a premature release of NO and a decrease in the therapeutic value of the foam dressing.

Entirely non-aqueous foams may be synthesized by substituting or complementing the polyhydrols with amino alcohols or alkanolamines. Examplary amino alcohols and alkanolamines may be found in U.S. Pat. No. 5,859,285, the disclosure of which is incorporated herein in its entirety. The alkanolamines may chemically store $CO_2$ on their amine groups, and this $CO_2$ may be released by heating. The alkanolamines may be dissolved in a polar solvent, preferably a diol or a triol, and contacted with $CO_2$ to form carbamates. In some embodiments, the polar solvent may be the polyol itself that can be the soft segment in the foam dressing.

The carbamate solution may be used to react with polyisocyanate to form the polyurethane foams. The carbamates may act as catalysts in foam formation, thereby avoiding the necessity of using other catalysts.

While any suitable alkanolamines may be used to produce carbamates, in some embodiments, the carbamates may be produced by using the following alkanolamines: 2-(2-aminoethylamino)ethanol, (3-[(2-aminoethyl)amino)]propanol), (2-[(3-aminopropyl)amino]ethanol), (1-[(2-aminoethyl)amino]-2-propanol, (2-[(3-aminopropyl) methylamino]ethanol, 1-[(2-amino-1-methylethyl)amino]-2-propanol, 2-[((2-amino-2-methylpropyl)amino]-2-methyl-1-propanol, 2-[(4-amino-3-methylbutyl)amino]-2-methyl-1-propanol, 17-amino-3,6,9,12,15-pentaazaheptadecan-1-ol and/or 3,7,12,16-tetraazaoctadecane-1,18-diol, in particular those based on 2-(2-aminoethylamino)ethanol as alkanolamine. The carbamate solution can be further blended with polyhydroxyl or polyamine containing compounds that have been pre-charged with NO and as a result, possess single or multiple NO-releasing functional group.

In addition to chemically storing the $CO_2$ blowing agent in the above manner, physical blowing agents may also be used in foam production. Examples of physical blowing agents include: hydrohalo-olefin (See U.S. Patent Application Publication No. 20090099272, the contents of which are incorporated herein by reference in their entirety); alkanes, such as 2-methylbutane, pentane, heptanes (See U.S. Pat. No. 5,194,325, the contents of which are incorporated by reference in their entirety), and other inert, low-boiling compounds such as pentene and acetone. Carbon dioxide, including supercritical carbon dioxide, may be used as a physical blowing agent as well.

In some embodiments of the invention, provided are methods of forming multilayer wound dressings that include combining one or more polymeric layers, wherein one or more polymer layers may include a polymer matrix and NO-releasing polysiloxane macromolecules therein or thereon. The combining of polymeric layers may be achieved by any suitable method, but in some embodiments, the polymer layers are laminated to each other. Exemplary laminating techniques include ultrasonic welding, annealing with anhydrous organic solvents and application of a pressure sensitive adhesive.

The present invention will now be described in more detail with reference to the following examples. However, these examples are given for the purpose of illustration and are not to be construed as limiting the scope of the invention.

EXAMPLES

Example 1

Figure 7:
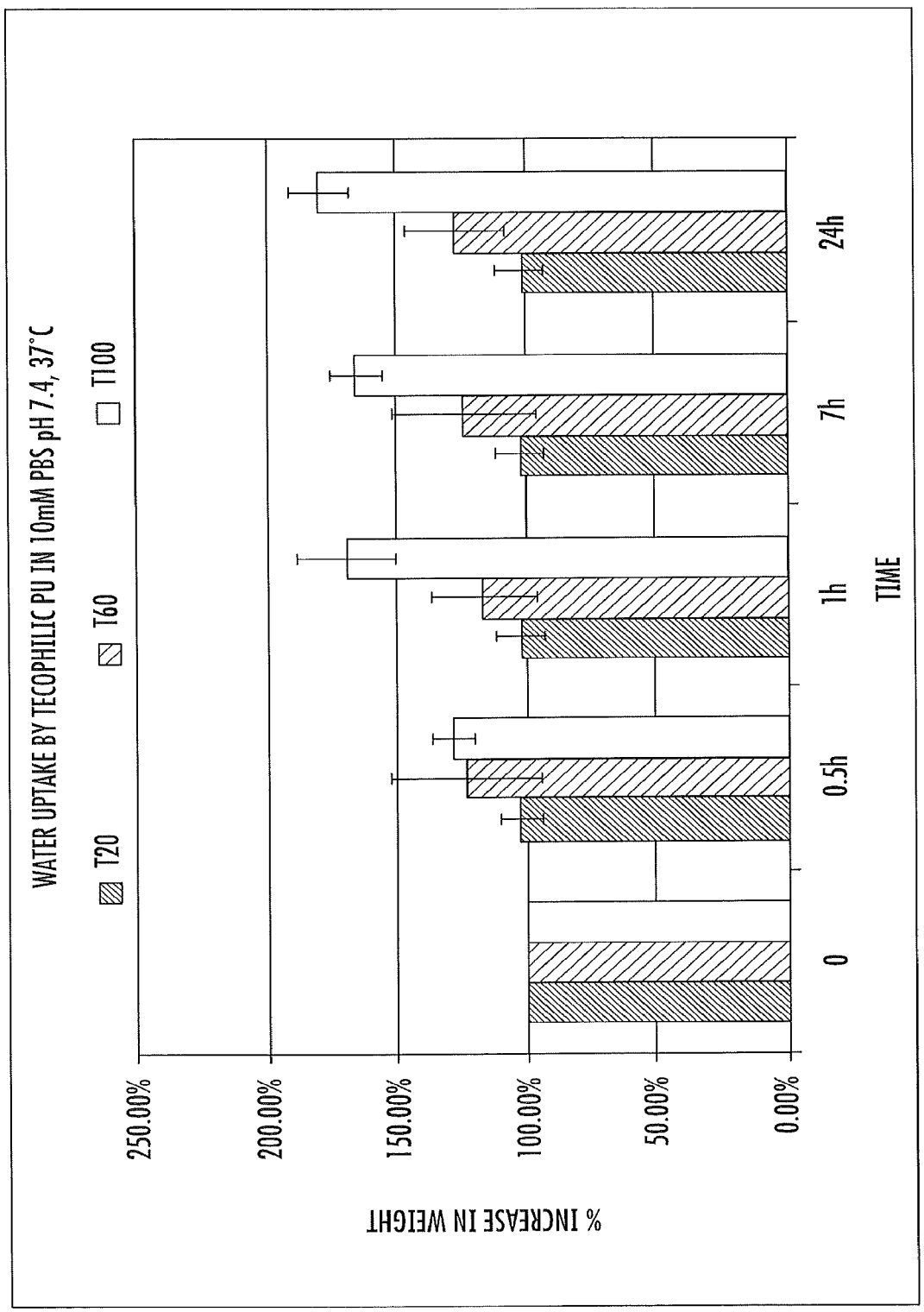
FIG. 7 shows water uptake of particular polyurethane polymer matrices over time.

The water uptake for three hydrophilic polyurethanes thin film dressings soaked in phosphate buffered saline at physiological temperature and pH is shown in FIG. 7. Tecophilic® Aliphatic thermoplastic polyurethanes HP-60D-20 ("T20"), HP-60D-60 ("T60"), and HP93A-100 ("T100") from Lubrizol, Inc. gradually displayed an increase in weight percentage overtime.

Example 2

Figure 8:
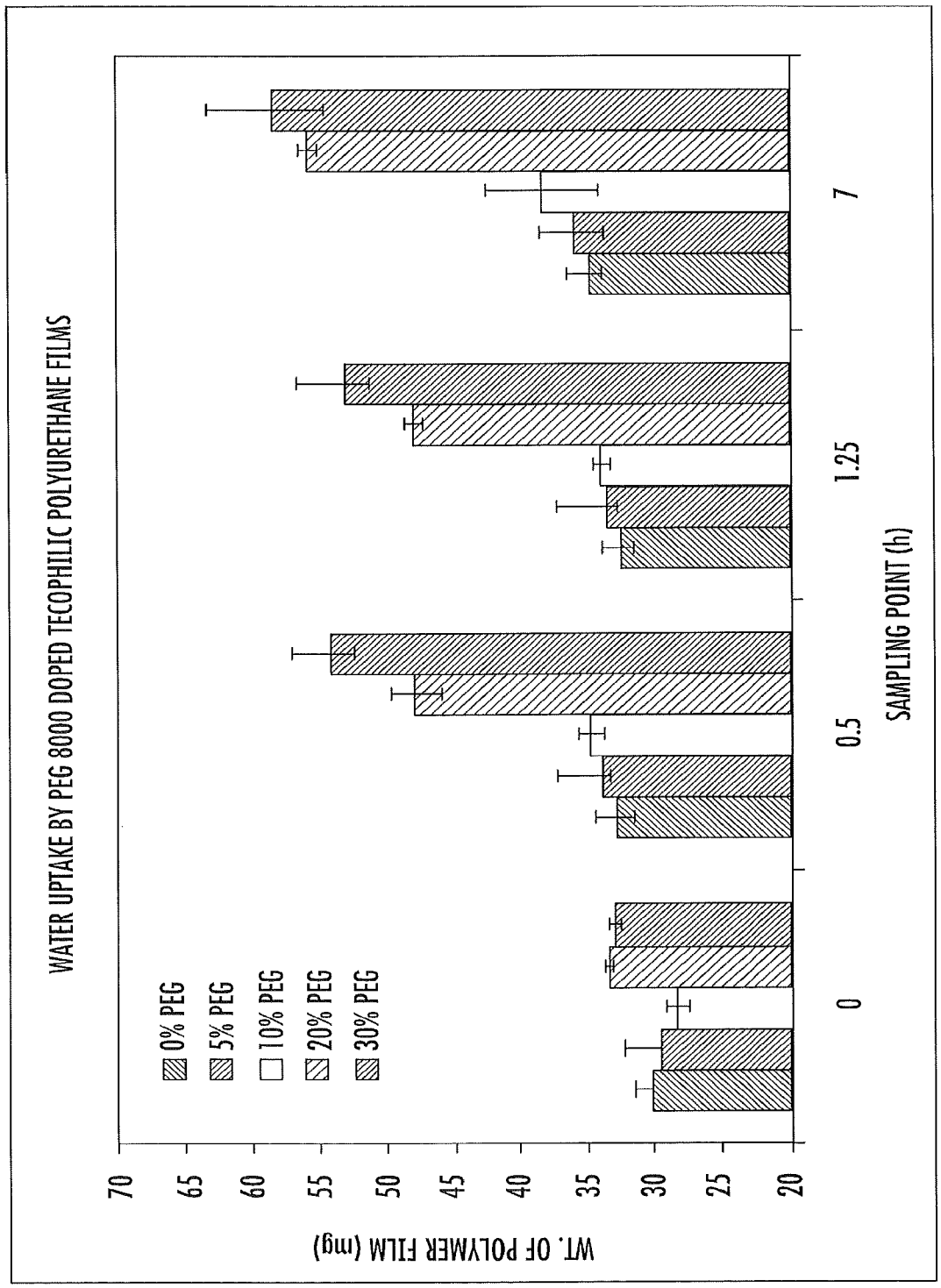
FIG. 8 shows water uptake for Tecophilic® Aliphatic thermoplastic polyurethane HP-60D-20 ("T20") loaded with increasing weight percent of poly(ethylene glycol) 8000 MW as a porogen.

The water uptake for Tecophilic® Aliphatic thermoplastic polyurethane HP-60D-20 ("T20") loaded with increasing weight percent of poly(ethylene glycol) 8000 MW as a porogen is shown in FIG. 8. The weight of the thin polymer films increases over time as the hydrophilicity of the polymer matrix is increased as a function of percent PEG loading.

Example 3

Figure 9:
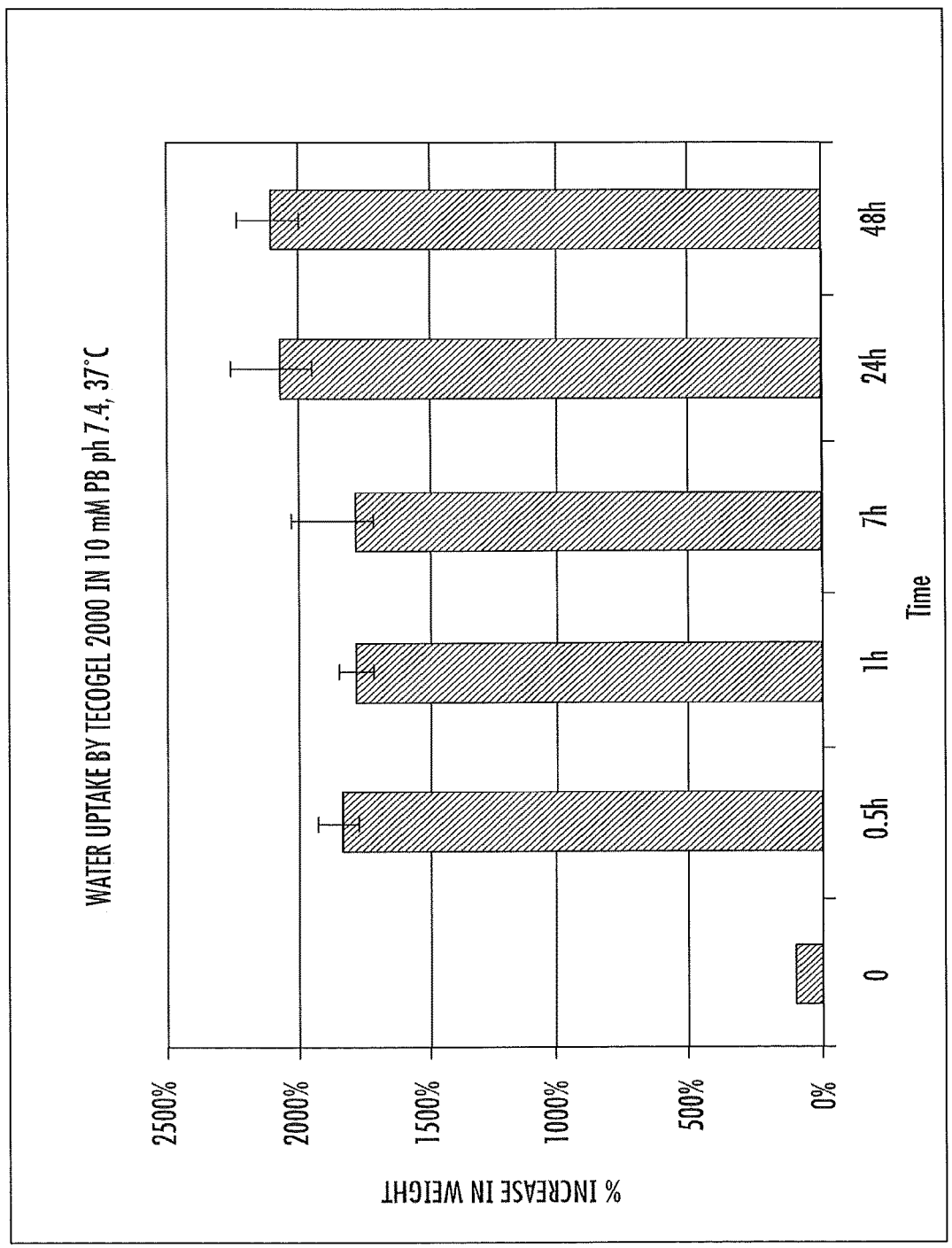
FIG. 9 shows the water uptake for Tecophilic® Hydrogel thermoplastic polyurethane TG-2000 solvent cast into polymer films thin film dressings and soaked in phosphate buffered saline at physiological temperature and pH.

The water uptake for Tecophilic® Hydrogel thermoplastic polyurethane TG-2000 solvent cast into polymer films thin film dressings and soaked in phosphate buffered saline at physiological temperature and pH is shown in FIG. 9. The weight of this superabsorbent polymer (SAP) rapidly increases upon exposure to moisture and swells to store water exceeding 2000 percent of its initial weight.

Example 4

Figure 10:
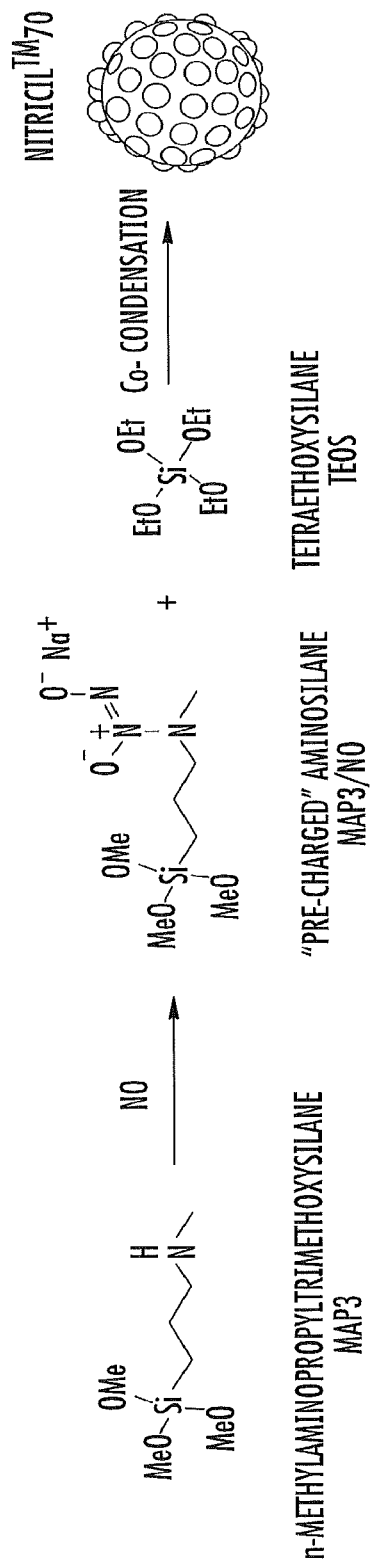
FIG. 10 illustrates the covalent storage of nitric oxide on the aminosilane N-methylaminopropyltrimethoxysilane as a diazeniumdiolate NO donor, followed by co-condensation with a backbone alkoxysilane, tetraethoxysilane, to form Nitricil™ composition 70.

FIG. 10 illustrates the covalent storage of nitric oxide on the aminosilane N-methylaminopropyltrimethoxysilane as a diazeniumdiolate NO donor, followed by co-condensation with a backbone alkoxysilane, tetraethoxysilane, to form Nitricil™ composition 70. The Nitricil™ 70 was incorporated with several of the hydrophilic polyurethanes from the previous examples and tested for their antimicrobial activity against a gram negative bacterium, *P. aeruginosa*. A $10^6$ innoculum of bacteria was deposited onto the surface of the NO-releasing wound dressings in an agar slurry and incubated for 24 h. The percent reduction of *P. aeruginosa* versus control polyurethane materials for each composition is shown in TABLE 1. The water uptake of the polymer and the corresponding NO-release kinetics from the Nitricil™ 70 directly affect the bactericidal activity.

TABLE 1

| Composition | Polymer | Nitricil 70% Loading (wt/wt) | % Reduction *P. aeruginosa* ATCC 15442 |
|---|---|---|---|
| A | T20 | 2.5 | 31 |
| B | T20 | 4 | 58 |
| C | T20 | 8 | >99.9999 |
| D | T20 | 10 | >99 |
| E | T20 | 14 | >99.9999 |
| F | T20 | 16 | >99.9999 |
| G | T20 | 20 | >99.9999 |
| H | T60 | 2.5 | 49 |
| I | T60 | 10 | >99.99 |
| J | T100 | 10 | 98.7 |
| K | T100 | 16 | ND |
| L | TG2000 | 10 | ND |

Example 5

Figure 11:
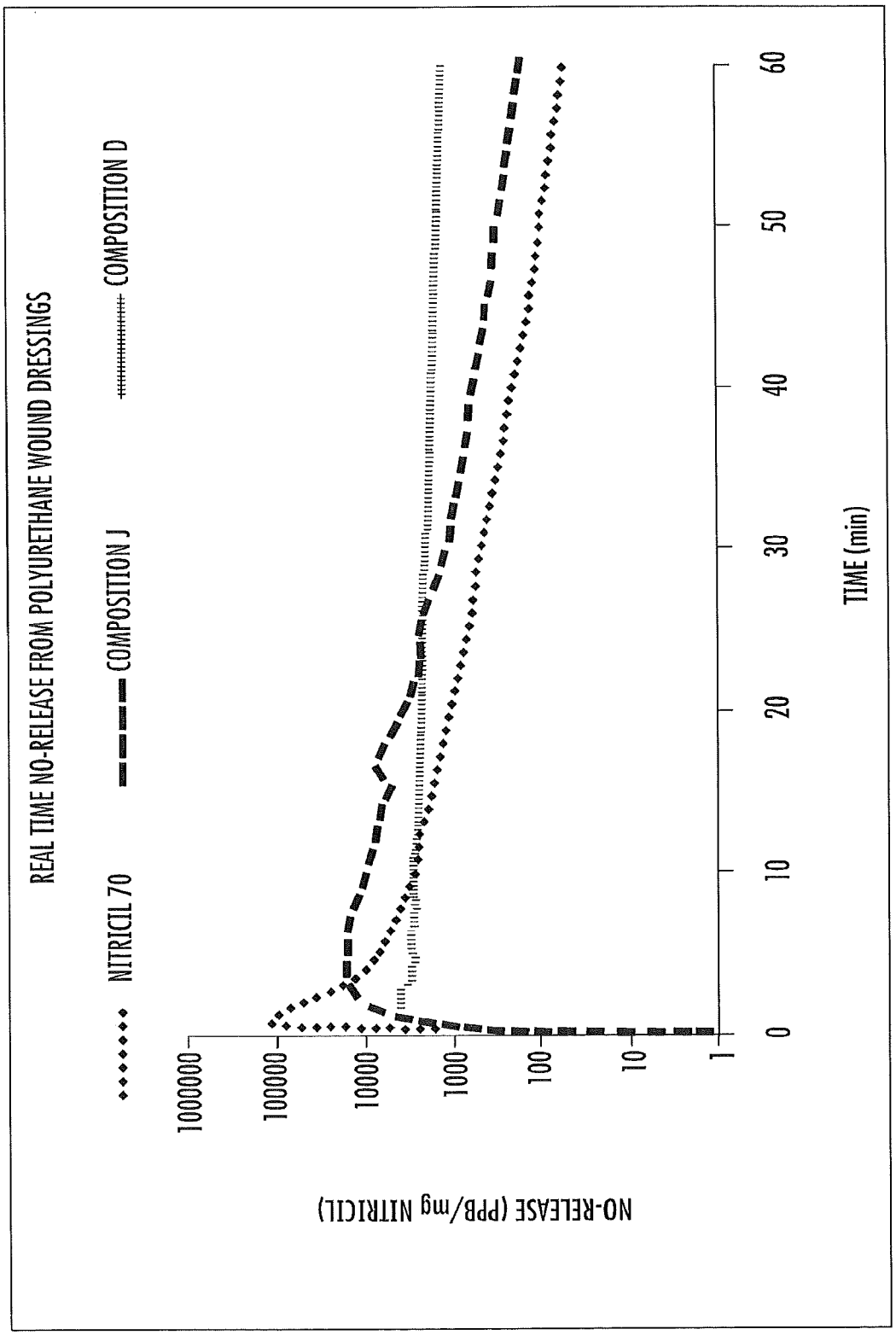
FIG. 11 depicts the chemiluminescent detection of NO release from Nitricil™ 70 silica particles free in solution, wound dressing Composition J, and wound dressing Composition D measured at physiological buffer, pH, and temperature.

FIG. 11 depicts the chemiluminescent detection of NO release from Nitricil™ 70 silica particles free in solution, wound dressing Composition J, and wound dressing Composition D measured at physiological buffer, pH, and temperature. The flux of NO release from the dressing surfaces are reported as PPB/mg of Nitricil™ loaded. As an example of how the polymer matrix governs resulting NO release, the initial levels of NO release from Composition D are 20× lower than the Nitricil™ alone. Composition D also maintains a more consistent level of NO-release over the first 60 min in comparison to Composition J at the equivalent 10% Nitricil™ loading ratio.

Example 6

Upon application to the wound, the polyurethane material of the wound dressing comes in contact with moisture in the wound bed. The polyurethane has some affinity for moisture due to the presence of polyether soft-chain segments in its structure, which results in a finite amount of water being taken up by the dressing. This inward diffusion of moisture within the polymer matrix leads to an increase in distance between the polymer chains and is observed as swelling of the polymer. The increasing distance between the chains and the concentration gradient between the water in the polymer and the bulk water in the wound bed, allow greater space of movement for the embedded silica particles. As a result, the particles may diffuse out of the polymer, with the smaller particles having a greater propensity. This phenomenon manifests itself as particle leaching.

Wound dressings comprising NO-releasing silica particles were engineered to minimize leaching upon exposure to moisture in the wound bed. The dressing polymer composition and silica loading wt/wt both affect the cumulative amount leached. Light scattering is a commonly used technique to characterize particle suspensions, particularly to measure the size and polydispersity of micrometer and nanometer particle sizes. In static light scattering mode, the time-averaged intensity of light scattered by a particle suspension is measured and is highly dependent upon the particle size, its concentration, and molecular weight. Thus, for a dilute suspension of fairly monodisperse particles, the time averaged light intensity should be directly proportional to the particle concentration, and the static light scattering is said to occur in the Rayleigh mode. A plot of scattering intensity vs. particle concentration yields a straight line and provide an accurate method for determining unknown particle concentrations that leach into solution from wound dressing prototypes.

To measure the potential concentrations of NO-releasing silica that accumulate in solution following incubation under physiologically buffered solutions for 24 and 48 hr, the light scattering intensity of each unknown particle sample was measured and converted to its concentration using a calibration curve. Nitric oxide-releasing silica-loaded polyurethane dressings were cut into three 0.75" x 0.75" square samples. The samples were weighed and placed into polypropylene vials and 10 mL of filtered phosphate buffered saline (PBS, 10 mM sodium dihydrogen phosphate, 137 mM NaCl, 2.3 mM KCl, pH 7.4) pre-warmed at 37° C. was added to each. The vials were then incubated in a water bath maintained at 37° C. After 24 hours, each of the vials were agitated and an aliquot was removed, which was transferred to a polystyrene cuvette. The static light scattering intensity of this aliquot was determined against filtered PBS as blank. The silica concentration of the leachate was then determined using the calibration curve to convert the obtained kcps value to mg/ml, and the obtained mg/ml values were expressed as a percentage of the amount of silica calculated to be initially loaded in the dressing sample.

The leaching values for representative compositions are shown below and illustrate the dependence on polymer hydrophilicity and homogeneity of the silica polyurethane composite: 5% w/v T20 in tetrahydrofuran, 80 mg silica/g polymer, slurry prepared via magnetic stirring (TABLE 2), 5% w/v T20 in tetrahydrofuran, 80 mg silica/g polymer, slurry prepared via sonication, (TABLE 3), 10% w/v T100 in tetrahydrofuran, 160 mg silica/g polymer, slurry prepared via magnetic stirring (TABLE 4), 10% w/v T20 in tetrahydrofuran, 160 mg silica/g polymer, slurry prepared via sonication (TABLE 5). All wound dressing polymers were solvent cast into thin films and dried under vacuum.

TABLE 2

| Day | Average | Stdev |
| --- | --- | --- |
| 1 | 11.01% | 1.58% |
| 2 | 9.23% | 1.37% |

TABLE 3

| Day | Average | Stdev |
| --- | --- | --- |
| 1 | 0.62% | 0.31% |
| 2 | 0.34% | 0.01% |

TABLE 4

| Day | Average | Stdev |
| --- | --- | --- |
| 1 | 21.1% | 6.73% |
| 2 | 23.72% | 9.14% |

TABLE 5

| Day | Average | Stdev |
| --- | --- | --- |
| 1 | 0.50% | 0.22% |
| 2 | 1.23% | 0.65% |

Example 7

Figure 12:
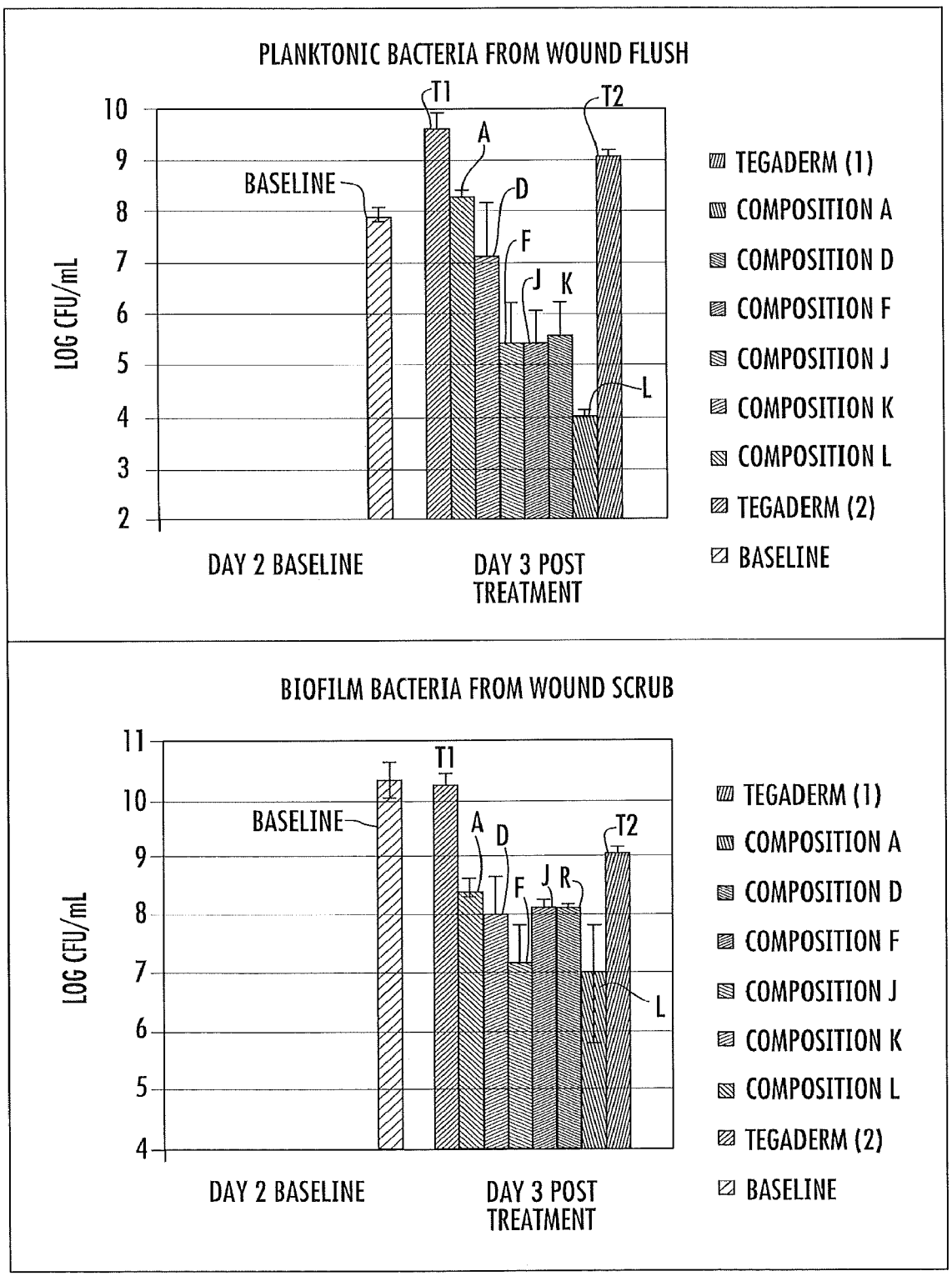
FIG. 12 shows the efficacy of various NO-releasing wound dressing compositions on both the levels of planktonic bacteria flushed from the wound and the levels of biofilm bacteria scrubbed from the wound are shown in comparison to Tegaderm™ covered controls.

*P. aeruginosa* biofilms were grown for 48 h in partial thickness wounds in a porcine animal model. After 2 days of growth, the baseline levels of bacteria from a flush of the wound with sterile buffer and a vigorous scrub of the wound with bacteria/tissue in sterile buffer were recorded. The planktonic bacteria were approximately $10^8$ CFU/mL and the biofilm embedded bacteria were above $10^{10}$ CFU/mL prior to treatment with NO-releasing wound dressings. The efficacy of various NO-releasing wound dressing compositions on both the levels of planktonic bacteria flushed from the wound and the levels of biofilm bacteria scrubbed from the wound are shown in comparison to Tegaderm™ covered controls in FIG. 12. The wound dressings comprising different polymer matrices and variable percentages of Nitricil™ loading elicited different outcomes when tested against an in vivo biofilm model.

Example 8

A medical grade, aliphatic polyether polyurethane that absorbs a small amount of water in the amount of 20% of its dry weight is combined with 14% w/w Nitricil™ 70 (nitric oxide-loaded precipitated silica) such that the Nitricil™ is permanently incorporated throughout the polyurethane matrix. The resulting polyurethane film device is transparent. The polymer blend is cast onto a transparent, siliconized PET release liner (FRA-308, Fox River Associates, LLC), which is pre-printed with a 1" square grid.

The testing performed to evaluate design and technical characteristics is summarized in the TABLE 6 below.

TABLE 6

| Performance Characteristic | Measured Value |
| --- | --- |
| Film Thickness | 98 ± 10 μm |
| Water Uptake [%] | 6.8 ± 2.9% |
| MVTR | 31 ± 16 g/m$^2$ · 24 h |
| Oxygen Permeability | 206 ± 91 mL O2 @ STP/100 in$^2$ |
| Tensile Strength | 9.57 ± 2.02 kg/in$^2$ |
| Residual solvent | 3.31 μL THF/g |
| Nitric Oxide Storage | 1.2 ± 0.1 μmoles NO/cm$^2$ |
| Leaching Analysis | <0.5% (<3 ppm) |

Figures 13A, 13B:
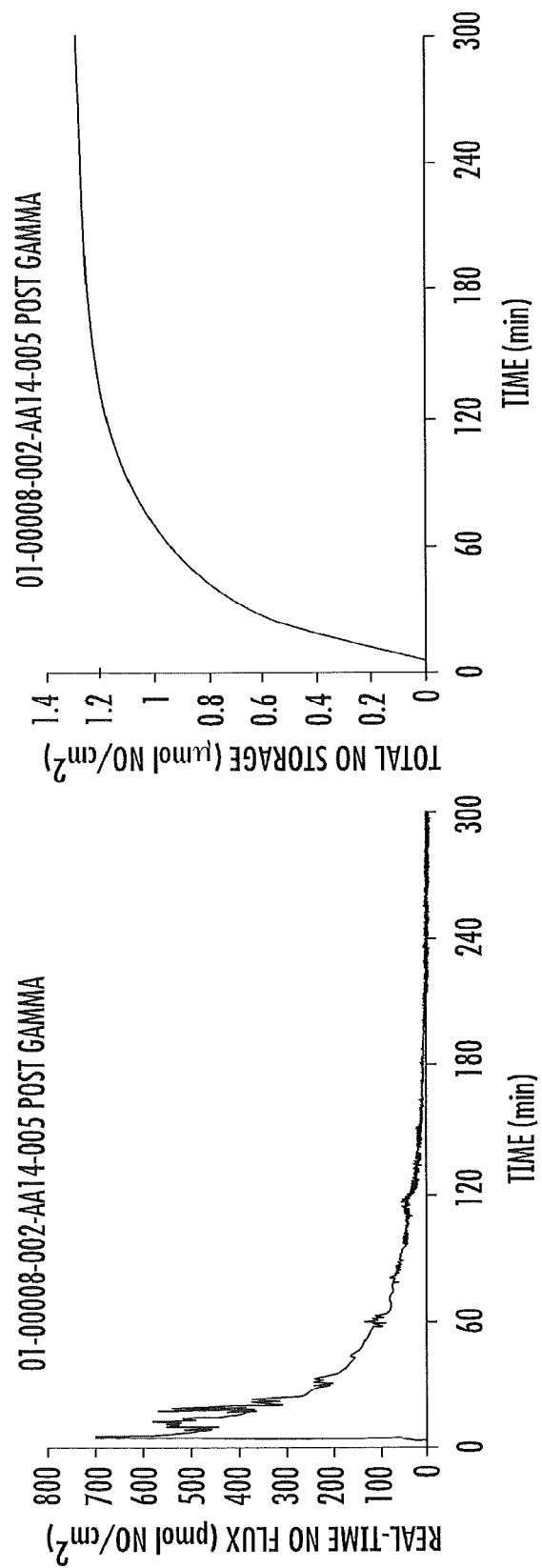
FIGS. 13A and 13B depict the NO behavior of the finished device soaked in buffer at physiological temperature and pH (37° C., 7.4).

Chemiluminescent detection of NO was used to characterize the nitric oxide release behavior from the polyurethane film device. The nitric oxide in the device is liberated upon exposure to moisture. FIGS. 13A and 13B depict the NO behavior of the finished device soaked in buffer at physiological temperature and pH (37° C., 7.4). The maximum flux at the device surface never exceeds 850 pmol NOcm$^{-2}$ s$^{-1}$ (FIG. 13A), and the total NO loaded in the device averaged 1.2+0.1 μmoles NO/cm$^{-2}$ (FIG. 13B) for all devices tested. The surface flux of nitric oxide from the proposed device was optimized to assist in providing a barrier to microbial penetration.

Example 9

Figure 14:
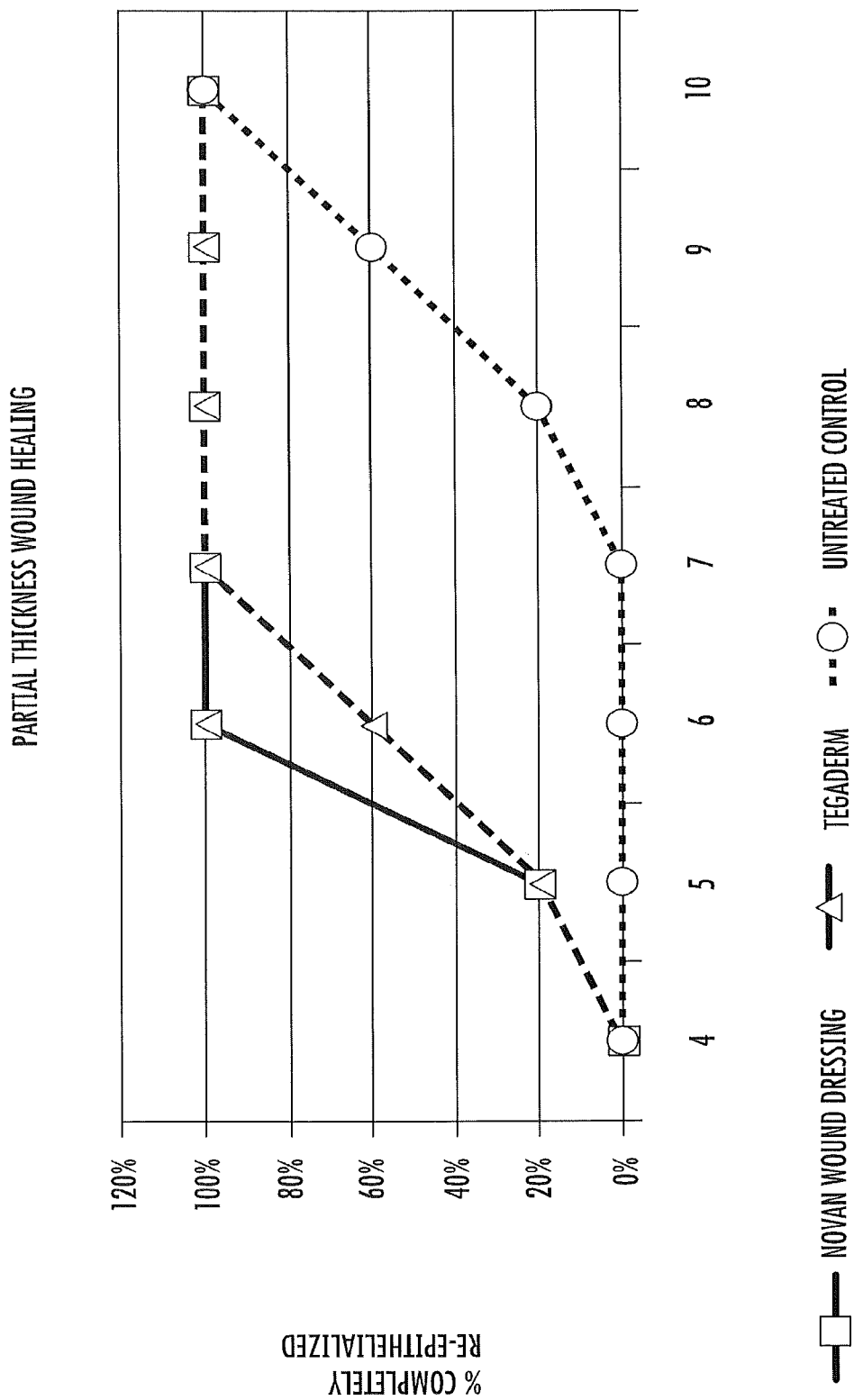
FIG. 14 depicts the % complete re-epitheliazation versus time for wound dressings according to embodiments of the invention in comparison to Tegaderm™ covered controls.

The nitric oxide-releasing wound dressing of Example 9 was used to treat partial thickness wounds in a porcine model. This study was designed to assess healing potential and whether or not the proposed device has a negative impact on normal wound repair in comparison to topical nitric oxide formulations previously reported (evidenced by delayed wound healing or significant erythema/edema). 160 rectangular wounds measuring 10 mm×7 mm×0.5 mm deep were divided into four treatment groups (40 wounds each). Wounds were dressed immediately after wounding and dressings were changed on days 2, 3, 5, and 7. Five wounds from each of the four groups were excised each day beginning on Day 4 after wounding and prepared according to the sodium bromide salt-split technique to assess epidermal migration. Epithelialization is considered complete (healed) if no defects or holes are present after the separation of the dermis and epidermis. Wounds in each of the groups were evaluated until 100% complete epithelialization was observed. The test materials were non-adherent to wound bed upon removal (no re-injury was observed) and none of the wounds from any of the treatment groups developed erythema, swelling or signs of infection. On Day 4, none of the treatment groups were completely re-epithelialized but Day 6, 100% of the wounds in the nitric oxide treated group were re-epithelialized in comparison to only 60% of the Tegaderm covered occlusive wound environment (FIG. 14). The average MVTR of the wound dressing in Example 9 across n=6 batches is 31±16 g/m$^2$-24h, representing a 9 fold greater MVTR than that of 3M Tegaderm Barrier Wound Dressing, measured under identical conditions (3.34 g/m$^2$-24h). Furthermore, the wound dressing in Example 9 has an MVTR <4% of the 840 g/m$^2$-24h value below which dressings are considered to be occlusive and is <1% of the 3000 to 5000 g/m$^2$-24h MVTR of damaged skin (Rennekampff, 1996). Untreated controls (air exposed) did not completely heal until Day 10 illustrating the importance of maintaining a moist wound environment.

Example 10

Testing has been performed by an independent laboratory, in accordance with Good Laboratory Practices, to evaluate the biocompatibility of the wound dressing in Example 9, as recommended by FDA's Blue Book Memo, G95-1, Use of International Standards ISO-10993, and Biological Evaluation of Medical Devices Part 1: Evaluation and Testing. Following are the tests that have been conducted along with a brief summary of results.

Cytotoxicity (in vitro): NON-TOXIC
MEM Elution extract was prepared from the dressing extracts and applied to mouse fibroblasts. Fibroblasts were scored for signs of cytotoxicity over a 72-hour test period. The wound dressing extract received a cytotoxicity score of 0 at all time points.

Sensitization (in vivo): NO SENSITIZATION
Normal saline and cotton seed oil extracts were prepared from the dressing extracts and tested using the Guinea Pig Maximization Sensitization Test. Both extracts elicited a 0% sensitization response.

Irritation/Intracutaneous Reactivity (in vivo): NON-IRRITANT
Normal saline and cotton seed oil extracts were prepared from the wound dressing and injected into rabbits. Injection sites were scored for reactivity over a 72-hour test period. For each extract, the difference between the mean reactivity score for the wound dressing extract and the mean reactivity score for the vehicle control was <1.0.

Systemic (Acute) Toxicity (in vivo): NON-TOXIC
Normal saline and cotton seed oil extracts were prepared from the wound dressing and injected into mice. Animals were observed for mortality and signs of pharmacological and toxicological effects over a 72-hour test period. Both extracts resulted in zero animal fatalities, zero animals exhibiting clinical signs of toxicity, and zero animals with body weight changes outside acceptable parameters.

Sub-acute (Sub-chronic) Toxicity (in vivo): NON-TOXIC
Normal saline and cotton seed oil extracts were prepared from the wound dressing and injected intravenously (saline) or intraperitoneally (oil) into mice once daily for 14 days. Animals were observed for mortality and signs of toxicity during the test period. There were no fatalities, no statistically significant weight differences between control and test animals, and no abnormal clinical signs noted for any of the animals during the test period. No clinically abnormal findings were noted during animal necropsies. Clinical chemistry and hematology data were not indicative of a pattern of toxicity.

Implantation (in vivo): NON-IRRITANT
Two implantation studies have been completed for the wound dressing in which pieces of were implanted intramuscularly in albino rabbits for either a one or four week study. At the end of the one-week implantation, the irritant ranking score for the wound dressing was calculated to be 1.2. At the end of the four-week implantation, the irritant ranking score for the wound dressing was calculated to be 2.6.

LAL Endotoxin Test for Pyrogens (in vitro, GMP): PASS
The kinetic chromogenic LAL test system was validated for use with the wound dressing. Samples from three production lots of the sterilized, finished device all contained <0.200 EU/device.

The wound dressing of Example 9 passed the requirements of all biocompatibility tests; thus it can be concluded that the product is biocompatible and non-toxic, providing a topical nitric oxide releasing solution with proven safety and effectiveness.

Example 11

This example describes a process of manufacturing NO-releasing flexible polyurethane foam starting from 100 kg of 2-(2-aminoethylamino) ethanol as a basis. The foam is prepared using Desmodur N-100 (22% NCO groups, Bayer Material Science, Pittsburgh, Pa.) as the polyisocyanate and Desmodur N- and Desmophen-R-221-75 (3.3% OH groups, Bayer Material Science, Pittsburgh, Pa.) as the polyol. Nitricil™-70 (Novan, Inc.) as an NO-releasing macromolecule is incorporated in the foam at a loading of 1% (w/w).

1. $CO_2$ is bubbled into the 100 kg 2-(2-aminoethylamino) ethanol to prepare 2-(2-aminoethylamino)ethanol carbamate
2. The 2-(2-aminoethylamino)ethanol carbamate is dissolved in 200 kg of Desmophen-R-221-75 polyol
3. Nitricil™-70, the blowing agent, and gel catalysts are added to the mixture (see U.S. Pat. No. 4,173,691)
4. The mixture is reacted with a stoichiometric excess of Desmodur N-100, under agitation and heating at 50° C.
5. The reaction mixture is cured at 50° C. to release the chemically bound $CO_2$.

Calculations for:
1. Amount of $CO_2$ needs to be bubbled
2. Amount of Desmodur N-100 be added
3. Amount of Nitricil™-70 to be added for a nominal 1% w/w loading Calculation for $CO_2$ Addition
There are two moles of NH per mole of 2-(2-aminoethylamino)ethanol. The number of moles of 2-(2-aminoethylamino) ethanol in 100 kg=961.54. The number of moles of NH=2*961.54=1923.07 moles. Thus, the weight of $CO_2$ required=1923.07 moles*44 g/mol=84.6 kg. A 1.2 fold excess gas to ensure complete conversion to carbamates. Thus, the amount of $CO_2$ required=101.52 kg.

Calculation for Catalyst Addition

Two types of catalyst are used in combination, a gel catalyst to accelerate the urethane formation reaction, and a blowing catalyst to reduce the rising time of the foam. The gel catalyst (e.g., stannous octoate) is present as 0.3 parts per 100 parts polyol (w/w). The blowing catalyst (e.g., antimony tris 2-ethylhexoate) is present as 0.3 parts per 100 parts polyol (w/w). Therefore, the catalyst calculation is based on the total mass of reacting hydroxyl compounds, and includes the hydroxyls in 2-(2-aminoethylamino) ethanol. Thus, the weight of gel catalyst=300 kg/100 kg*0.3=9 kg. The weight of blowing catalyst=9 kg.

Calculation for Desmodur N-100 Addition

Enough Desmodur N-100 needs to be added such that the NCO are adequate to react with OH in 2-(2-aminoethylamino) ethanol and in Desmophen. The equivalent of OH groups in Desmophen-R-221-75 (3.3% OH)=17*100/3.3=515. The moles of OH groups in 100 kg 2-(2-aminoethylamino)ethanol=961.54. The equivalents in 200 kg=200/515=0.388. The equivalent NCO groups in Desmodur N-100 (22% NCO)=42*100/22=191. The equivalents of NCO required for 1:1 reaction with 200 kg Desmophen-R-221–75=191*0.388=74.2 kg. The percent OH in 2-(2-aminoethylamino)ethanol=17/104=16.3%. The equivalent of OH groups=17*100/16.3=104. The equivalents in 100 kg=100/104=0.9615. The equivalents of NCO required for 1:1 reaction=0.9615*191=183.65 kg. Thus, the total required=183.65 6+74.2=257.83 kg. A 2% excess is used to ensure complete reaction. Therefore, the Desmodur N-100 total requirement=1.02*257.83=262.985 kg.

Calculation for Nitricil™-70

The total reactant weight (not including $CO_2$)=262.985 kg (Desmodur N-100)+200 kg (Desmophen-R-221-75 polyol)+100 kg (2-(2-aminoethylamino) ethanol)+18 kg (weight of blowing catalyst and gel catalyst)=580.985 kg. Thus, 1% Nitricil™-70=5.81 kg.

SUMMARY

| Material | Amount to be used (kg) |
| --- | --- |
| 2-(2-aminoethylamino) ethanol | 100 |
| Desmophen-R-221-75 | 200 |
| Desmodur N-100 | 262.985 |
| Nitricil ™-70 | 5.81 |
| Stannous octoate | 9 |
| Antimony tris 2-ethylhexoate | 9 |

In the drawings and specification, there have been disclosed typical embodiments of the invention and, although specific terms are employed, they are used in a generic and descriptive sense only and not for purposes of limitation, the scope of the invention being set forth in the following claims.

We claim:

1. A wound dressing comprising:
a polymer matrix comprising a foam, and
nitric oxide (NO)-releasing polysiloxane macromolecules within the polymer matrix,
wherein the NO-releasing polysiloxane macromolecules are NO-releasing particles that have a molar mass of at least 500 Da and a diameter in a range of 0.1 nm to 100 μm,
wherein the polymer matrix comprises a polymer selected from the group consisting of acrylate polymers, acrylic acid polymers, copolymers thereof and blends thereof, and
wherein the wound dressing is non-toxic and stably stores NO.

2. The wound dressing of claim 1, wherein the NO-releasing polysiloxane macromolecules comprise N-diazeniumdiolate functional groups.

3. The wound dressing of claim 1, wherein the NO-releasing polysiloxane macromolecules comprise S-nitrosothiol functional groups.

4. The wound dressing of claim 1, wherein the NO-releasing polysiloxane macromolecules are present at a concentration in a range of about 0.1 to about 20 weight percent of the polymer matrix.

5. The wound dressing of claim 1, wherein the polymer matrix comprises at least one selected from the group consisting of: hydrophilic polyacrylates, co-polymers of carboxymethylcellulose and acrylic acid, poly(acrylic acid), poly(acrylic acid) derivatives, acrylic acid copolymers, methacrylic acid, methacrylic acid derivatives, and methacrylic acid copolymers.

6. The wound dressing of claim 1, further comprising a water-soluble porogen selected from the group consisting of sodium chloride, sucrose, glucose, lactose, sorbitol, xylitol, polyethylene glycol, polyvinylpyrrollidone, polyvinyl alcohol and mixtures thereof.

7. The wound dressing of claim 1, further comprising at least one therapeutic agent selected from the group consisting of antimicrobial compounds, anti-inflammatory agents, pain-relievers, immunosuppressants, vasodilators, wound healing agents, anti-biofilm agents and mixtures thereof.

8. The wound dressing of claim 1, wherein the wound dressing is a single layer with a thickness ranging from 10 to 5000 microns.

9. The wound dressing of claim 1, wherein the wound dressing is substantially transparent.

10. The wound dressing of claim 1, wherein nitric oxide is released from a surface of the wound dressing at a flux in a range of 0.1 pmol NO $cm^{-2}$ to 100 pmol NO $cm^{-2}$.

11. The wound dressing of claim 1, wherein nitric oxide is stored in the wound dressing in an amount in a range of 100 pmol NO $cm^{-2}$ to 1000 pmol NO $cm^{-2}$.

12. The wound dressing of claim 1, wherein nitric oxide is stored in the wound dressing in an amount in a range of 1 nmol NO $cm^2$ to 10 μmol NO $cm^{-2}$.

13. The wound dressing of claim 1, wherein the wound dressing comprises:
a first layer that, when applied to a wound bed, contacts the wound bed and is non-interactive with the wound bed, and
a second layer on the first layer.

14. The wound dressing of claim 13, wherein the first layer comprises at least one therapeutic agent and is devoid of NO-releasing macromolecules, and wherein the second layer comprises the polymer matrix having the NO-releasing polysiloxane macromolecules therein.

15. The wound dressing of claim 1, wherein at least 95% of the NO is retained in the wound dressing after one week at 25° C.

16. The wound dressing of claim 1, wherein greater than 98% of the NO-releasing polysiloxane macromolecules are retained in the wound dressing after incubation of the wound dressing in phosphate buffered saline at pH 7.4 for 48 hours at 37° C.

17. A method for treating a wound comprising applying a wound dressing of claim 1 to a wound.

18. The method of claim 17, further comprising debriding the wound prior to applying the wound dressing.

19. The method of claim 17, further comprising performing negative pressure wound therapy to the wound prior to, concurrently with or after applying the wound dressing.

20. The method of claim 19, whereby a negative pressure wound therapy device and the wound dressing are configured as one device.

21. The method of claim 17, further comprising treating the wound with an anti-biofilm agent prior to or in combination with the application of the wound dressing.

22. A method of forming a wound dressing, comprising: combining NO-releasing polysiloxane macromolecules and at least one monomer; and
polymerizing the at least one monomer to form a polymer matrix comprising the NO-releasing polysiloxane macromolecules, wherein the NO-releasing polysiloxane macromolecules are NO-releasing particles that have a molar mass of at least 500 Da and a diameter in a range of 0.1 nm to 100 µm, wherein the polymer matrix comprises a foam, and wherein the polymer matrix comprises a polymer selected from the group consisting of acrylate polymers, acrylic acid polymers, copolymers thereof and blends thereof.

23. The method of claim 22, wherein the monomer is polymerized by photocuring.

24. The method of claim 22, wherein the polymerizing the at least one monomer occurs by a method comprising depositing a liquid monomer, the NO-releasing polysiloxane macromolecules and an initiator; and polymerizing the liquid monomer.

25. The method of claim 22, wherein combining the NO-releasing polysiloxane macromolecules and the at least one monomer comprises dispersing the NO-releasing macromolecules in a mixture of foam forming monomers;
wherein polymerizing the at least one monomer to form a polymer matrix comprises polymerizing the foam forming monomers to form a polymer, and foaming the polymer to form the polymer matrix.

26. The method of claim 22, wherein combining the NO-releasing polysiloxane macromolecules and the at least one monomer comprises reacting functional groups on the NO-releasing macromolecules with at least one foam forming monomer;
wherein polymerizing the at least one monomer to form a polymer matrix comprises polymerizing the foam forming monomers to form a polymer, and foaming the polymer to form the polymer matrix.

27. The method of claim 22, wherein the foam is formed by the use of a blowing agent selected from at least one of the group consisting of carbon dioxide, hydrohalo-olefins and alkanes.

28. The method of claim 27, wherein the blowing agent comprises carbon dioxide generated from carbamates that are formed from alkanolamines selected from at least one of the group consisting of 2-(2-aminoethylamino)ethanol, (3-[(2-aminoethyl)amino)]propanol), (2-[(3-aminopropyl)amino]ethanol), (1-[(2-aminoethyl)amino]-2-propanol, (2-[(3-aminopropyl)methylaminol]ethanol, 1-[(2-amino-1-methylethyl)amino]-2-propanol, 2-[((2-amino-2-methylpropyl)amino]-2-methyl-1-propanol, 2-[(4-amino-3-methylbutyl)amino]-2-methyl-1-propanol, 17-amino-3,6,9,12,15-pentaazaheptadecan-1-ol and 3,7,12,16-tetraazaoctadecane-1,18-diol.

29. The method of claim 22, wherein the polymer matrix comprises at least one selected from the group consisting of: hydrophilic polyacrylates, co-polymers of carboxymethylcellulose and acrylic acid, poly(acrylic acid), poly(acrylic acid) derivatives, acrylic acid copolymers, methacrylic acid, methacrylic acid derivatives, and methacrylic acid copolymers.

30. A wound dressing kit, comprising one or more of
a first wound dressing that releases low concentrations of nitric oxide over 0 to 7 days in the range of 0.5 pmol NO cm$^{-2}$ s$^{-1}$ to 20 pmol NO cm$^{-2}$ s$^{-1}$ upon initial application to a patient;
a second wound dressing that releases intermediate concentrations of nitric oxide over 0 to 7 days in the range of 20 pmol NO cm$^{-2}$ s$^{-1}$ to 1000 pmol NO cm$^{-2}$ s$^{-1}$ upon initial application to the patient; and
a third wound dressing that releases high levels of nitric oxide for 0 to 48 hours in the range of 1 nmol NO cm$^{-2}$ s$^{-1}$ to 1 µmol NO cm$^{-2}$ s$^{-1}$ upon initial application to the patient,
wherein each of the wound dressings comprises a polymer matrix and NO-releasing polysiloxane macromolecules within the polymer matrix, wherein the NO-releasing polysiloxane macromolecules are NO-releasing particles that have a molar mass of at least 500 Da and a diameter in a range of 0.1 nm to 100 µm, wherein the polymer matrix comprises a foam, wherein the polymer matrix comprises a polymer selected from the group consisting of acrylate polymers, acrylic acid polymers, copolymers thereof and blends thereof, and wherein each wound dressing is non-toxic and can stably store nitric oxide.

31. The wound dressing kit of claim 30, wherein the second wound dressing further includes an anti-inflammatory agent.

32. The wound dressing kit of claim 30, wherein the third wound dressing further includes an anti-microbial agent.

33. The wound dressing kit of claim 30, wherein the polymer matrix comprises at least one selected from the group consisting of: hydrophilic polyacrylates, co-polymers of carboxymethylcellulose and acrylic acid, poly(acrylic acid), poly(acrylic acid) derivatives, acrylic acid copolymers, methacrylic acid, methacrylic acid derivatives, and methacrylic acid copolymers.

34. The wound dressing of claim 1, wherein the NO-releasing polysiloxane macromolecules comprise N-diazeniumdiolate functional groups and wherein the polymer matrix comprises at least one selected from the group consisting of:
hydrophilic polyacrylates, co-polymers of carboxymethylcellulose and acrylic acid, poly(acrylic acid), poly(acrylic acid) derivatives, acrylic acid copolymers, methacrylic acid, methacrylic acid derivatives, and methacrylic acid copolymers.

35. The method of claim 22, wherein the NO-releasing polysiloxane macromolecules are present at a concentration in a range of about 0.1 to about 20 weight percent of the polymer matrix.

36. The wound dressing kit of claim 30, wherein the NO-releasing polysiloxane macromolecules are present at a concentration in a range of about 0.1 to about 20 weight percent of the polymer matrix for each of the first, second, and third wound dressings.

* * * * *

UNITED STATES PATENT AND TRADEMARK OFFICE
CERTIFICATE OF CORRECTION

| | |
|---|---|
| PATENT NO. | : 11,583,608 B2 |
| APPLICATION NO. | : 15/887649 |
| DATED | : February 21, 2023 |
| INVENTOR(S) | : Stasko et al. |

It is certified that error appears in the above-identified patent and that said Letters Patent is hereby corrected as shown below:

In the Specification

Column 8, Line 26: Please correct "80 As" to read --80 µm. As--

Signed and Sealed this
Eighteenth Day of July, 2023

Katherine Kelly Vidal
*Director of the United States Patent and Trademark Office*